(12) United States Patent
Fujisaki et al.

(10) Patent No.: US 10,524,640 B2
(45) Date of Patent: Jan. 7, 2020

(54) ENDOSCOPIC TREATMENT INSTRUMENT, TREATMENT INSTRUMENT UNIT, AND TREATMENT SYSTEM

(71) Applicant: OLYMPUS CORPORATION, Hachioji-shi, Tokyo (JP)

(72) Inventors: Ken Fujisaki, Sagamihara (JP); Hiroyuki Araki, Hachioji (JP); Kazuhiro Yoshida, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 285 days.

(21) Appl. No.: 15/449,627

(22) Filed: Mar. 3, 2017

(65) Prior Publication Data
US 2017/0172389 A1  Jun. 22, 2017

Related U.S. Application Data

(63) Continuation of application No. PCT/JP2015/072534, filed on Aug. 7, 2015.

(30) Foreign Application Priority Data

Sep. 5, 2014  (JP) .................................. 2014-181739

(51) Int. Cl.
*A61B 1/00* (2006.01)
*A61B 17/24* (2006.01)
(Continued)

(52) U.S. Cl.
CPC ........ *A61B 1/00154* (2013.01); *A61B 1/0016* (2013.01); *A61B 1/00082* (2013.01);
(Continued)

(58) Field of Classification Search
CPC ..... A61B 1/00154; A61B 1/233; A61B 1/015; A61B 1/07; A61B 1/00163; A61B 1/05;
(Continued)

(56) References Cited

U.S. PATENT DOCUMENTS 5,545,121 A * 8/1996 Yabe .................. A61B 1/00142
206/363
7,559,925 B2  7/2009 Goldfarb et al.
(Continued)

FOREIGN PATENT DOCUMENTS

DE   202006017173 U1   2/2007
DE   102011107614 A1   1/2013
(Continued)

OTHER PUBLICATIONS

Apr. 17, 2018 extended Search Report issued in European Patent Application No. 15838306.7.
(Continued)

*Primary Examiner* — Timothy J Neal
(74) *Attorney, Agent, or Firm* — Oliff PLC

(57) ABSTRACT

An endoscopic treatment instrument includes a guide sheath. The guide sheath includes a second distal end, which has an inside diameter to insert the insertion portion therethrough so that the distal end of the insertion portion is configured to protrude relative to the second distal end. The guide sheath is inserted through the guide pipe so that the second distal end is configured to protrude relative to the first distal end of the guide pipe.

24 Claims, 24 Drawing Sheets

(51) Int. Cl.
  *A61M 1/00* (2006.01)
  *A61B 1/015* (2006.01)
  *A61B 1/05* (2006.01)
  *A61B 1/07* (2006.01)
  *A61B 1/233* (2006.01)
  *A61B 17/00* (2006.01)
  *A61B 17/22* (2006.01)
  *A61B 90/00* (2016.01)
  *A61B 17/34* (2006.01)
  *A61B 90/30* (2016.01)

(52) U.S. Cl.
  CPC ...... *A61B 1/00094* (2013.01); *A61B 1/00142* (2013.01); *A61B 1/00163* (2013.01); *A61B 1/00172* (2013.01); *A61B 1/015* (2013.01); *A61B 1/05* (2013.01); *A61B 1/07* (2013.01); *A61B 1/233* (2013.01); *A61B 17/24* (2013.01); *A61M 1/0064* (2013.01); *A61B 17/3421* (2013.01); *A61B 90/36* (2016.02); *A61B 2017/0038* (2013.01); *A61B 2017/0046* (2013.01); *A61B 2017/00331* (2013.01); *A61B 2017/00367* (2013.01); *A61B 2017/00455* (2013.01); *A61B 2017/00477* (2013.01); *A61B 2017/00991* (2013.01); *A61B 2017/22051* (2013.01); *A61B 2017/246* (2013.01); *A61B 2090/036* (2016.02); *A61B 2090/0811* (2016.02); *A61B 2090/306* (2016.02); *A61B 2090/3614* (2016.02); *A61B 2217/005* (2013.01); *A61M 2210/0681* (2013.01)

(58) Field of Classification Search
  CPC ............ A61B 1/00094; A61B 1/00082; A61B 1/00142; A61B 1/00135; A61B 17/24; A61B 2017/246
  See application file for complete search history.

(56) References Cited

U.S. PATENT DOCUMENTS

| | | |
|---|---|---|
| 2004/0059363 A1 | 3/2004 | Alvarez et al. |
| 2007/0282305 A1 | 12/2007 | Goldfarb et al. |
| 2007/0293727 A1 | 12/2007 | Goldfarb et al. |
| 2008/0097400 A1 | 4/2008 | Chang et al. |
| 2008/0154207 A1* | 6/2008 | Hardin ............... A61M 25/09 604/164.13 |
| 2008/0167527 A1 | 7/2008 | Slenker et al. |
| 2011/0288477 A1 | 11/2011 | Ressemann et al. |
| 2011/0301415 A1* | 12/2011 | Motai ............... A61B 1/00154 600/114 |
| 2012/0004502 A1 | 1/2012 | Weitzner et al. |
| 2012/0071856 A1 | 3/2012 | Goldfarb et al. |
| 2014/0018732 A1 | 1/2014 | Bagaoisan et al. |

FOREIGN PATENT DOCUMENTS

| | | |
|---|---|---|
| JP | 2005532869 A | 11/2005 |
| JP | 2010515529 A | 5/2010 |
| JP | 2013540502 A | 11/2013 |
| WO | 2008124482 A2 | 10/2008 |
| WO | 2013-119258 A1 | 8/2013 |
| WO | 2014/072977 A1 | 5/2014 |

OTHER PUBLICATIONS

Mar. 7, 2017 International Preliminary Report on Patentability issued in International Patent Application No. PCT/JP2015/072534.
Nov. 2, 2015 International Search Report issued in International Patent Application No. PCT/JP2015/072534.
May 7, 2019 Office Action issued in Japanese Application No. 2017-007631.
Jun. 5, 2019 Office Action issued in Chinese Application No. 201580047576.6.
Nov. 5, 2019 Office Action issued in Japanese Patent Application No. 2017-007631.

* cited by examiner

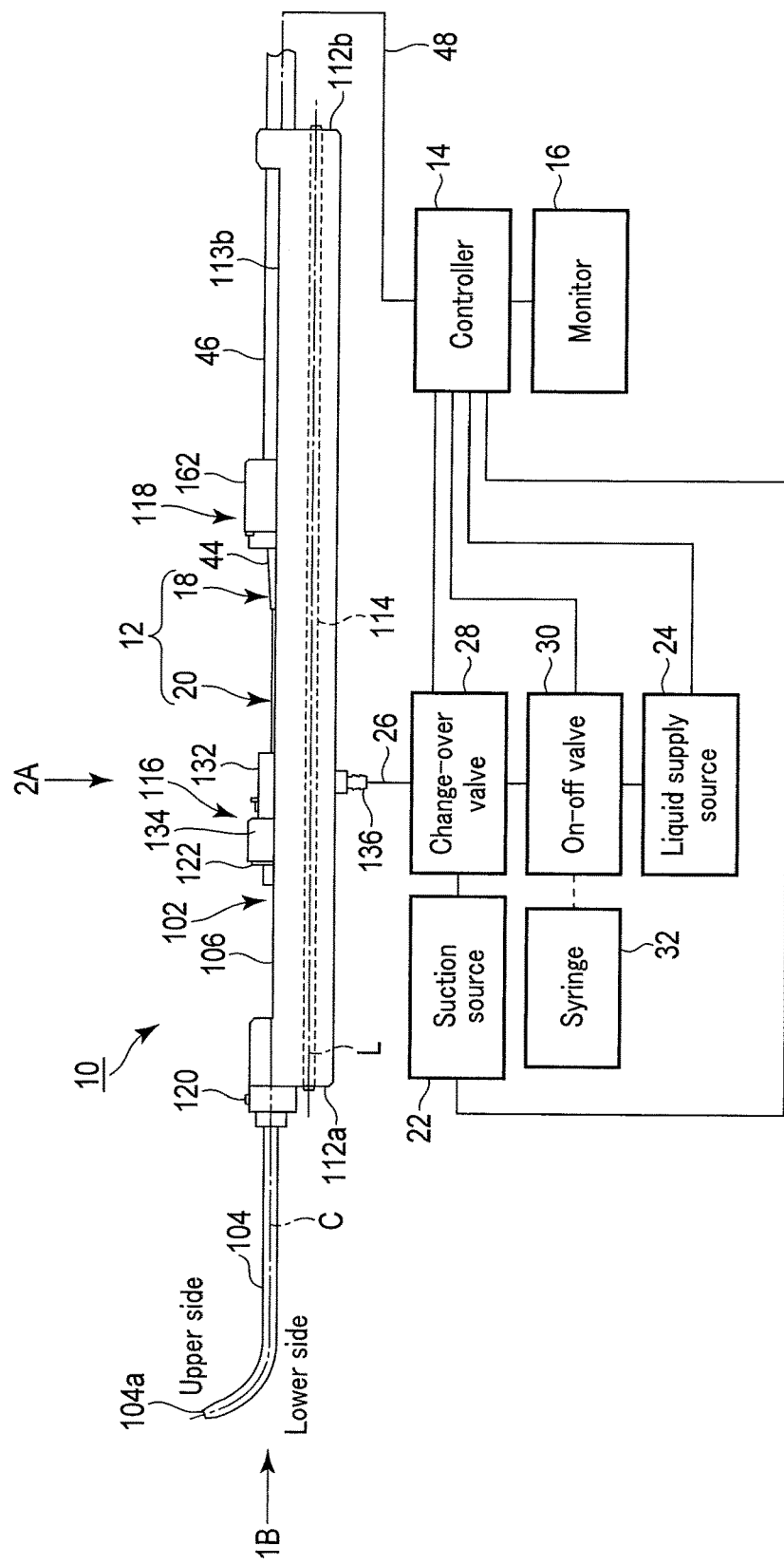
F I G. 1A

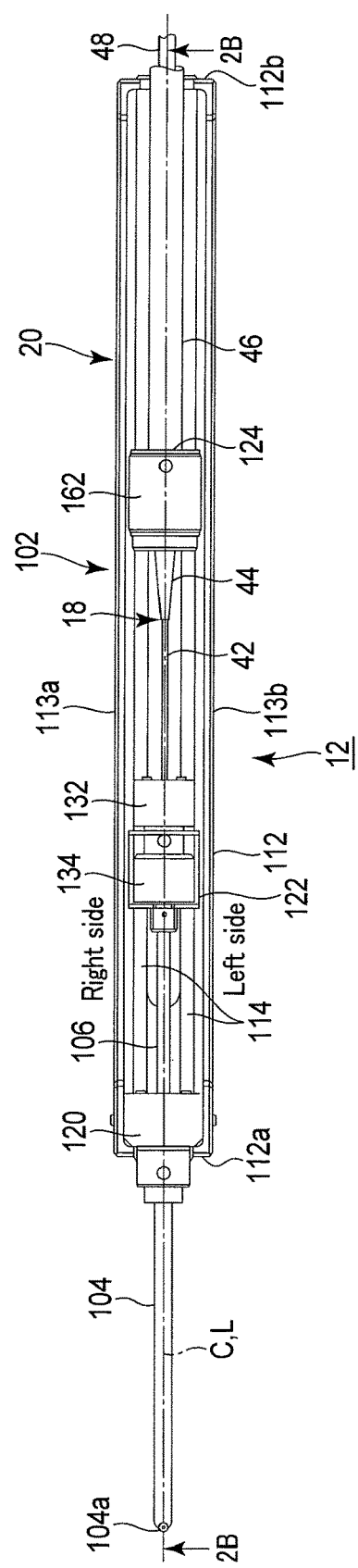
F I G. 2A

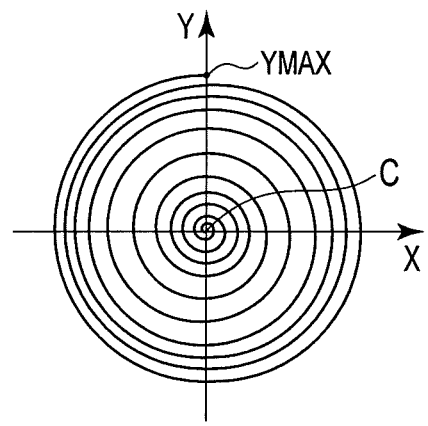
F I G. 4A
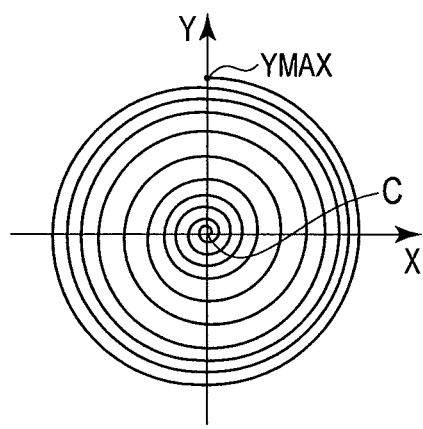
F I G. 4B

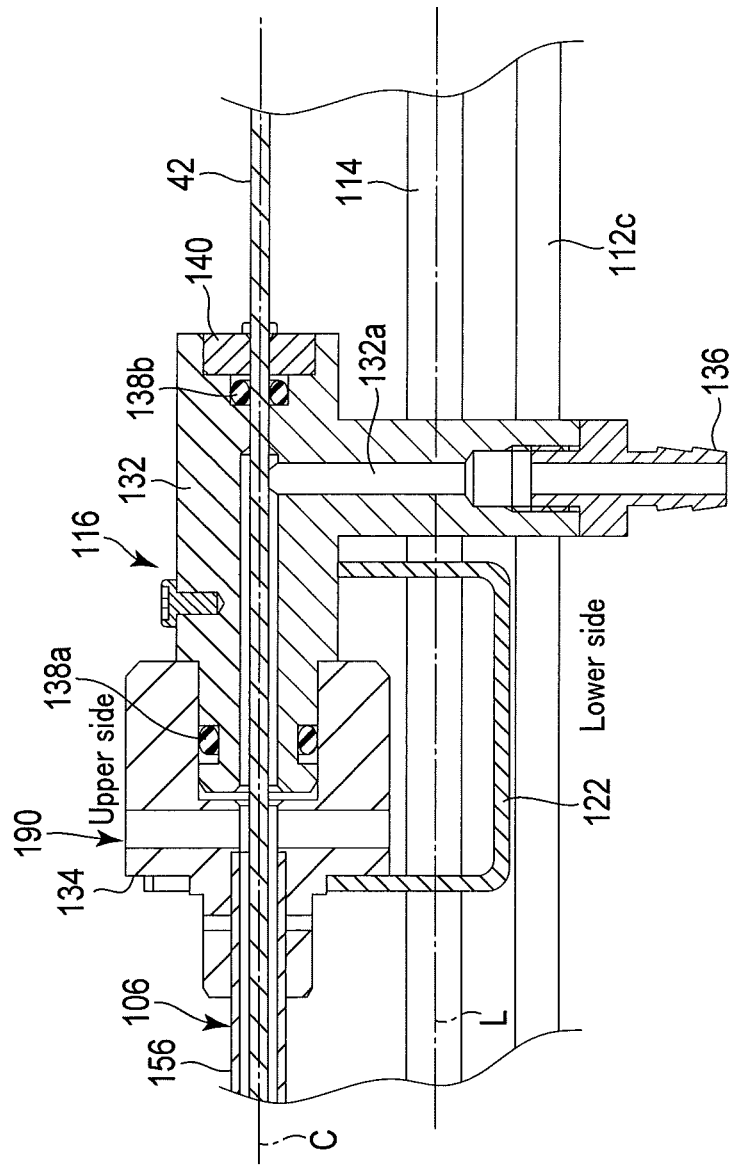
F I G. 6B

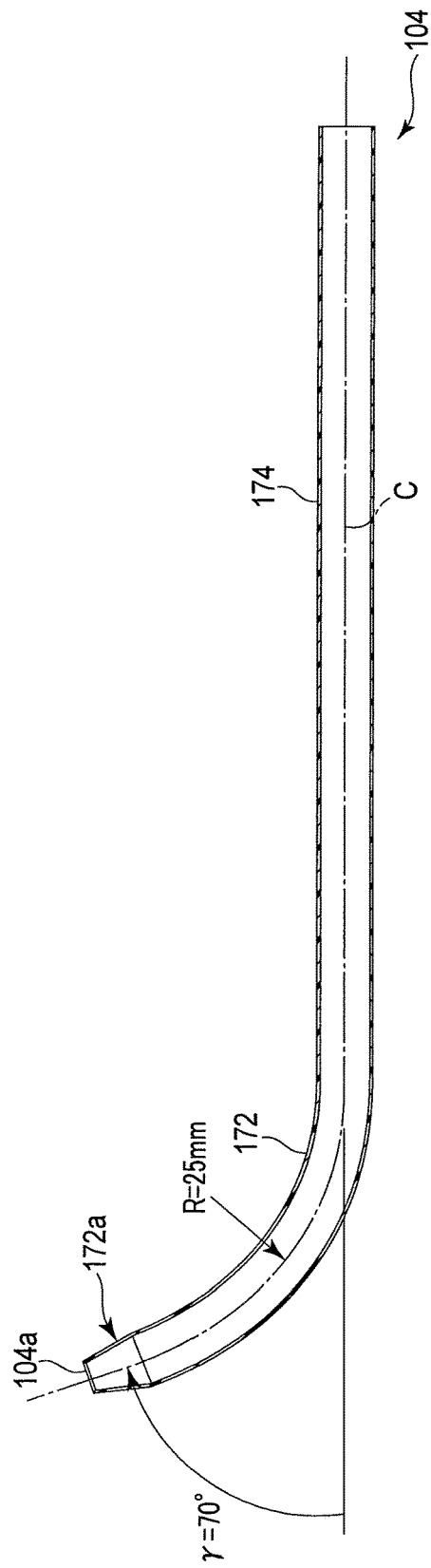
F I G. 8E

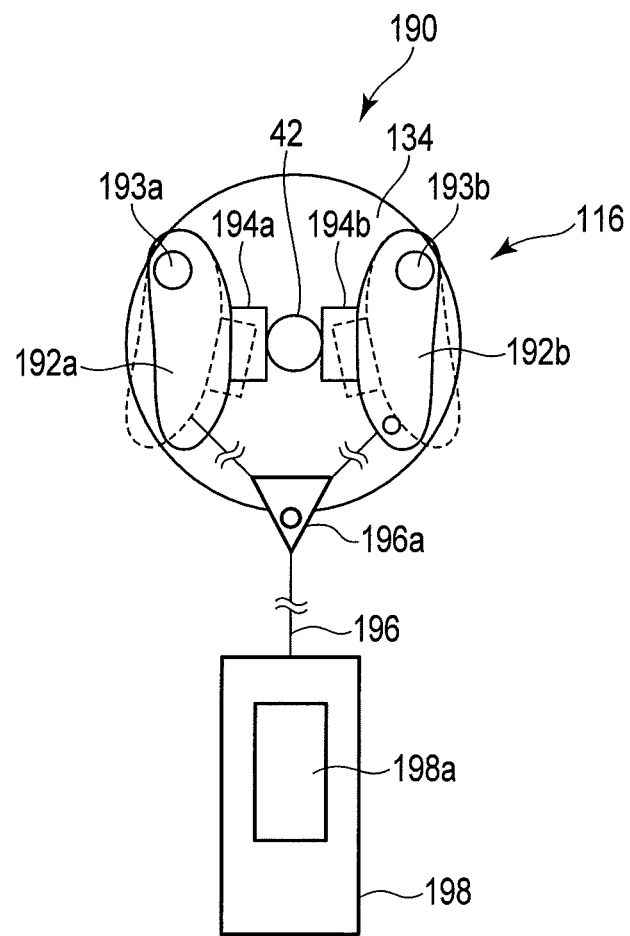
F I G. 10

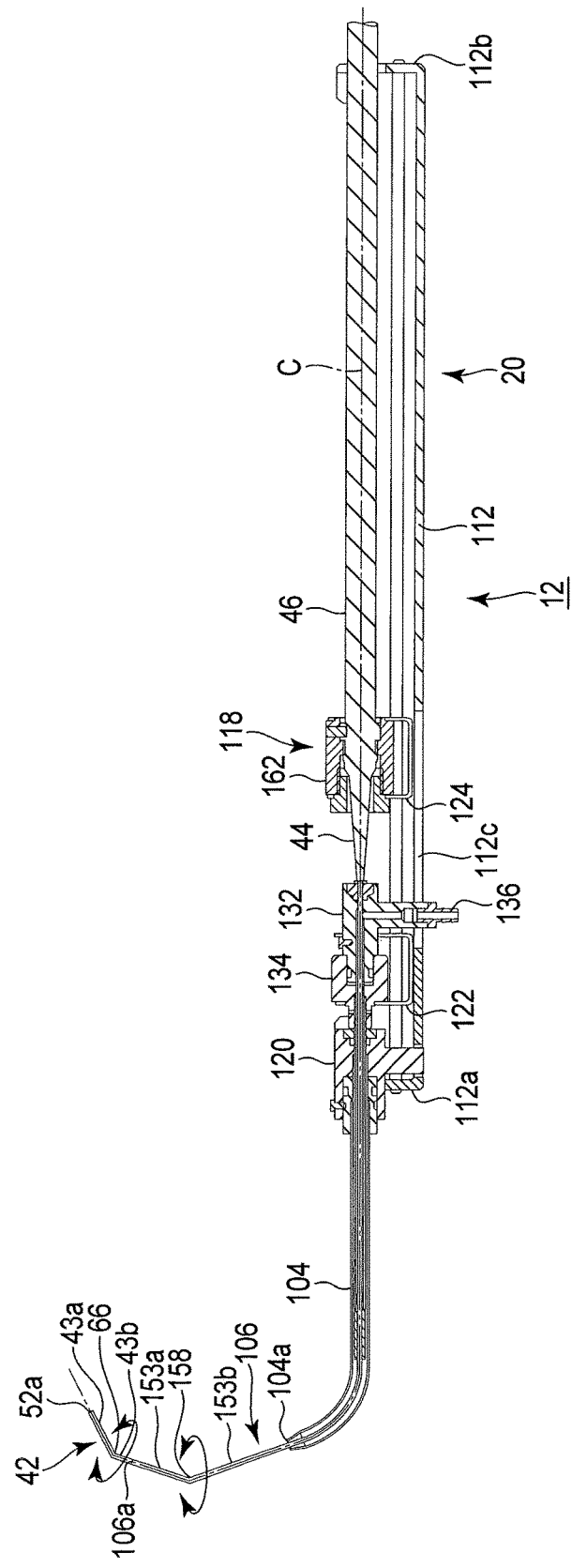
F I G. 14

ENDOSCOPIC TREATMENT INSTRUMENT, TREATMENT INSTRUMENT UNIT, AND TREATMENT SYSTEM

CROSS-REFERENCE TO RELATED APPLICATIONS

This application is a Continuation Application of PCT Application No. PCT/JP2015/072534, filed Aug. 7, 2015 and based upon and claiming the benefit of priority from prior Japanese Patent Application No. 2014-181739, filed Sep. 5, 2014, the entire contents of all of which are incorporated herein by reference.

BACKGROUND OF THE INVENTION

1. Field of the Invention

This invention relates to an endoscopic treatment instrument used together with an endoscope, a treatment instrument unit having the treatment instrument, and a treatment system.

2. Description of the Related Art

For example, U.S. Pat. No. 7,559,925 has disclosed a treatment instrument in which a light guide fiber is inserted through a guide pipe. This treatment instrument guides the light guide fiber to a paranasal sinus while visually recognizing, through the skin and bone of a patient, light emitted from the distal end of the light guide fiber. That is, the position of the distal end of the light guide fiber in the nasal cavity is estimated on the basis of the light emitted from the distal end of the light guide fiber.

BRIEF SUMMARY OF THE INVENTION

According to an aspect of the invention, there is provided an endoscopic treatment instrument used together with an endoscope including an insertion portion through which an observation optical system is inserted, the endoscopic treatment instrument including: a guide pipe which has a first distal end and through which the insertion portion is inserted so that a distal side of a distal end of the insertion portion and a distal side of the first distal end are observable through the first distal end by the observation optical system or so that the distal side of the distal end of the insertion portion is observable by the observation optical system while the distal end of the insertion portion is protruded relative to the first distal end; and a guide sheath which has a second distal end and which has an inside diameter to insert the insertion portion therethrough so that the distal end of the insertion portion is configured to protrude relative to the second distal end and which is inserted through the guide pipe so that the second distal end is configured to protrude relative to the first distal end of the guide pipe.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1A is a schematic diagram of a treatment system according to a first embodiment;

FIG. 2A is a schematic top view showing the endoscopic treatment instrument unit of the treatment system viewed from the direction of an arrow 2A in FIG. 1A;

FIG. 4A is a schematic diagram showing a scanning path which is scanned with illumination light actuated by an actuator and emitted from an illumination optical fiber from a position indicated by a reference sign C to a position indicated by a reference sign YMAX when a subject is observed by an observation optical system of the insertion portion of the endoscope of the endoscopic treatment instrument unit according to the first embodiment;

FIG. 4B is a schematic diagram showing a scanning path which is scanned with the illumination light emitted from the illumination optical fiber from the position indicated by the reference sign YMAX to the position indicated by the reference sign C;

FIG. 6B is a schematic diagram showing, in an enlarged form, the endoscopic treatment instrument unit at a position indicated by the reference sign 6B in FIG. 2B in the vicinity of a first operation element;

FIG. 8E is a schematic longitudinal sectional view showing a modification of the guide pipe shown in FIG. 8A;

FIG. 10 is a schematic diagram showing an example of an interlock mechanism which is disposed in the handle unit of the treatment instrument unit of the treatment system according to the first embodiment and which switches to an interlocked state to interlock the operations of the first operation element and a second operation element and to a non-interlocked state for independent operations;

FIG. 14 is a schematic longitudinal sectional view showing how the distal end of the guide sheath including the crooked portion is protruded relative to the distal end of the guide pipe of the treatment instrument unit of the treatment system according to the first embodiment, the distal end of the insertion portion of the endoscope including the crooked portion is protruded relative to the distal end of the guide sheath which is protruded relative to the distal end of the guide pipe, and the distal end of the guide pipe including the crooked portion and the distal end of the insertion portion of the endoscope including the crooked portion are turnable on their crooked portions;

DETAILED DESCRIPTION OF THE INVENTION

Figure 1B:
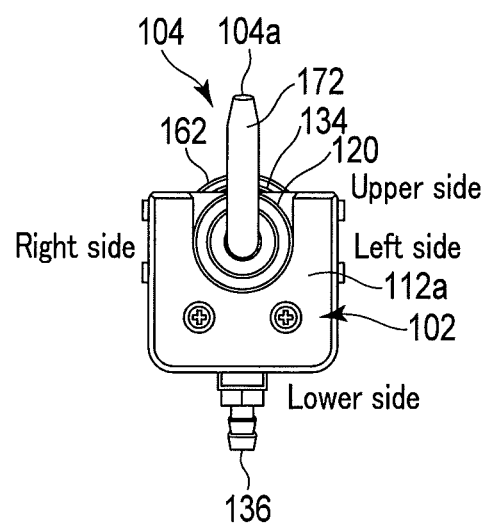
FIG. 1B is a schematic front view showing an endoscopic treatment instrument unit of the treatment system viewed from the direction of an arrow 1B in FIG. 1A.

Hereinafter, embodiments of this invention will be described with reference to the drawings.

The first embodiment is described with reference to FIG. 1A to FIG. 14.

As shown in FIG. 1A, a treatment system (endoscopic system) 10 according to this embodiment includes a treatment instrument unit (endoscope insertion assist unit) 12, a controller 14, and a monitor 16. The treatment instrument unit 12 includes an endoscope 18 and a treatment instrument (endoscopic insertion assist instrument) 20.

A suction source 22 and a liquid supply source (liquid sending source) 24 are connectable to the treatment instrument 20. A change-over valve 28 such as a three-way cock is provided between the end of a tube 26 extending from the treatment instrument 20, the suction source 22, and the liquid supply source 24. Thus, a user can selectively use the suction source 22 and the liquid supply source 24 for the treatment instrument 20 by operating the change-over valve 28. It is also preferable that an on-off valve 30 such as a three-way cock to which a syringe 32 can be removably connected is provided for medication, for example, between the change-over valve 28 and the liquid supply source 24. The change-over valve 28 and the on-off valve 30 may be electromagnetically operated by turning an unshown switch connected to the controller 14 or may be manually switched.

A liquid supplied from the liquid supply source 24 can be suitably selected. The liquid supply source 24 can supply a physiological saline, for example, to clean an affected part in a paranasal sinus inside a nose. Moreover, the liquid supply source 24 can supply a chemical to treat the affected part. As the chemical, steroid or an antibacterial agent is mainly administered. Here, instead of simply administering the chemical, temperature-responding gel which increases viscosity at about the body temperature may be used to extend the time in which the chemical remains in the affected part. In this case, if the chemical is administered to the affected part, the viscosity of the chemical increases due to the body temperature of a patient, so that the chemical does not easily flow out of the affected part and remains for a longer time. That is, if such a chemical is administered to the affected part, the chemical is easily retained in the affected part. As the suction source 22, it is possible to use, for example, a suction device provided on the wall of an operation room as it is. For example, viscous matter present in the paranasal sinus or around the affected part in a nasal cavity can be removed by actuating the suction source 22. When the affected part and the parts therearound are cleaned with the physiological saline, this cleaning liquid can be removed together with the viscous matter.

Figure 2B:
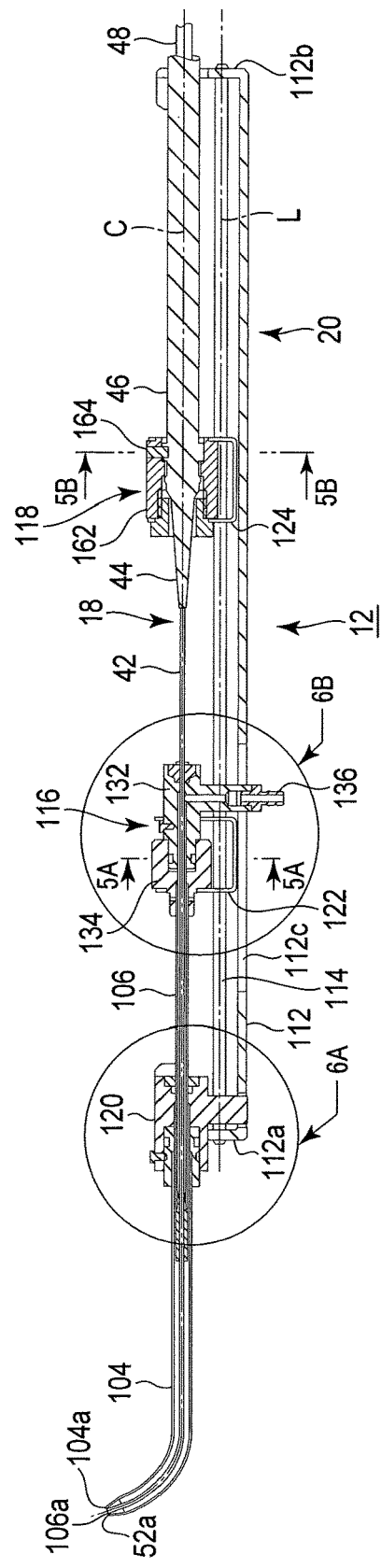
FIG. 2B is a schematic longitudinal sectional view of the endoscopic treatment instrument unit along the arrow 2B-2B line in FIG. 2A.

As shown in FIG. 2A and FIG. 2B, the endoscope 18 includes an insertion portion 42, an antibreak 44, a support portion 46, and a cable 48. The insertion portion 42 has a length of, for example, about 200 mm, and is formed to protrude, for example, about 100 mm relative to a distal end 104a of a later-described guide pipe 104. The insertion portion 42 preferably has a small outside diameter of, for example, about 1.0 mm to 2 mm. Thus, the endoscope 18 may be any type such as a fiber type or an image pickup device type such as a CCD or a CMOS, but a scanning type is preferably used. By using such an endoscope 18, it is possible to have a small outside diameter of the insertion portion 42 and obtain satisfactory image quality.

The scanning endoscope 18 is known and is therefore not described in detail. Meanwhile, the internal structure of a distal end 42a of the insertion portion 42 is formed as shown in FIG. 3.

Figure 3:
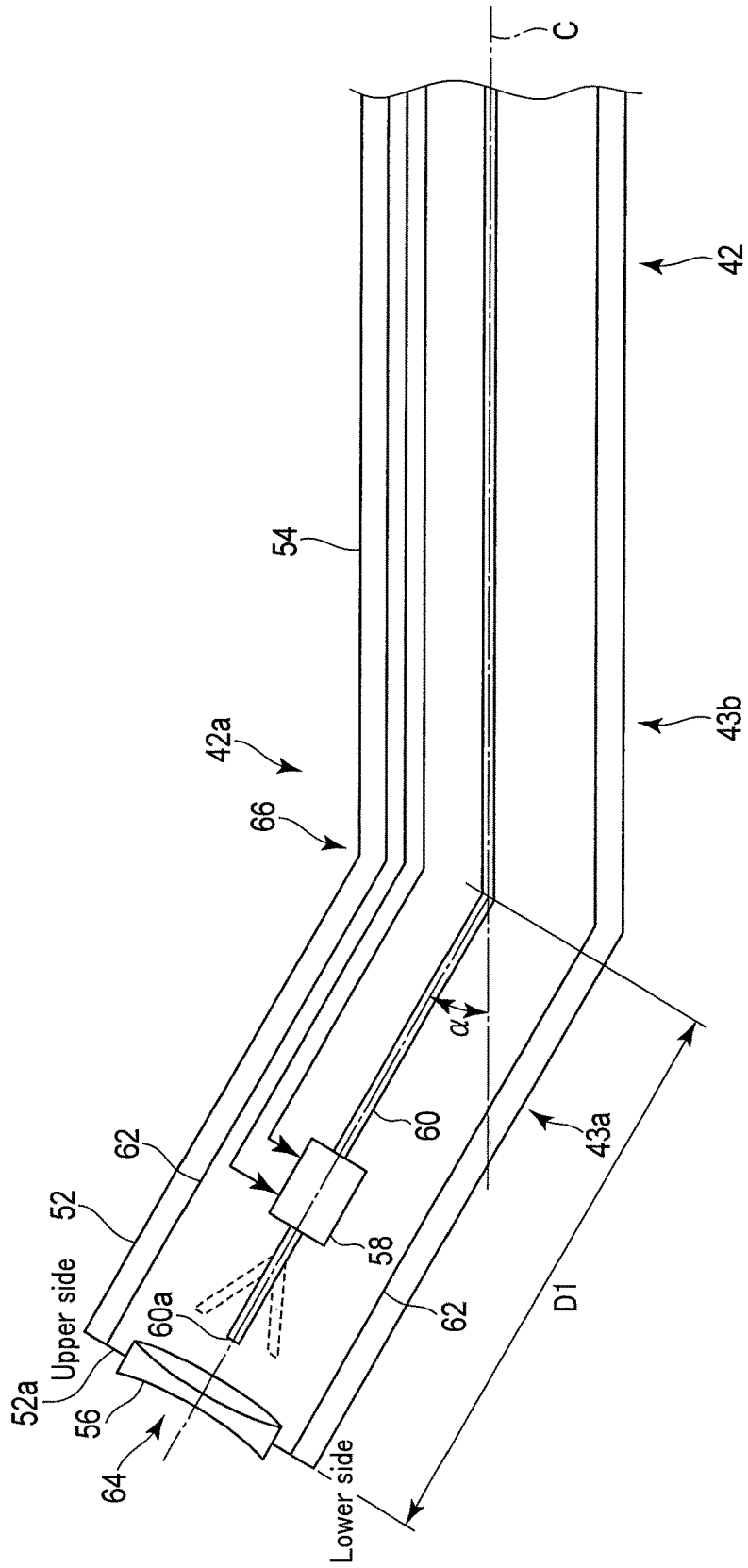
FIG. 3 is a schematic longitudinal sectional view showing the distal end of an insertion portion of an endoscope of the treatment instrument unit of the treatment system according to the first embodiment.

As shown in FIG. 3, the insertion portion 42 of the scanning endoscope 18 includes a distal hard portion 52, a flexible pipe 54, an illumination window 56, an actuator 58, an illumination fiber 60, and light receiving fibers 62. Among these components, the illumination window 56, the actuator 58, the illumination fiber 60, and the light receiving fibers 62 constitute an observation optical system 64. That is, the observation optical system 64 is provided inside the insertion portion 42. In the observation optical system 64, the actuator 58, the illumination fiber 60, and the light receiving fibers 62 are optically and/or electrically connected to the controller 14 shown in FIG. 1A.

The controller 14 shown in FIG. 1A controls the observation optical system 64 of the endoscope 18. The controller 14 controls the operation of the actuator 58. The controller 14 has an unshown light source of, for example, white light, and properly causes light for observation to enter the illumination fiber 60. The controller 14 images the light received by the light receiving fibers 62.

The distal hard portion 52, the illumination window 56, the actuator 58, the distal end of the illumination fiber 60, and the distal ends of the light receiving fibers 62 are provided at the distal end 42a of the insertion portion 42.

The distal ends of the illumination window 56 and the light receiving fibers 62 are fixed to a distal end face (distal end) 52a of the distal hard portion 52. The distal ends of the light receiving fibers 62 are fixed around the illumination window 56 at proper intervals.

The distal hard portion 52 is provided with the actuator 58 on the proximal side of the illumination window 56. The actuator 58 supports the distal end (a part closer to the proximal side than the most distal end) of the illumination fiber 60. The actuator 58 is shaken by the controller 14, for example, in a spiral manner shown in FIG. 4A and FIG. 4B. Thus, a distal end 60a of the illumination fiber 60 is spirally shaken in accordance with the operation of the actuator 58. Specifically, the controller 14 actuates the actuator 58, and moves illumination light emitted from the distal end of the illumination fiber 60 from a position indicated by a reference sign C in FIG. 4A to a position indicated by a reference sign YMAX. The controller 14 also actuates the actuator 58, and shakes the illumination light emitted from the distal end of the illumination fiber 60 from the position indicated by the reference sign YMAX in FIG. 4B to the position indicated by the reference sign C as soon as the illumination light reaches the position indicated by the reference sign YMAX. Therefore, the surface of the subject is spirally scanned with the illumination light through the distal end of the illumination fiber 60 and the illumination window 56.

The light receiving fibers 62 receive reflected light from the subject, and guide the light to the controller 14. The controller 14 shown in FIG. 1A images the light received by the light receiving fibers 62, and displays the formed image on the monitor 16 connected to the controller 14.

As shown in FIG. 3, on the proximal side of the distal hard portion 52, the flexible pipe 54 extends to this proximal side. The length of the distal hard portion 52 is, for example, about 10 mm. Thus, the flexible pipe 54 accounts for the most of the total length of the insertion portion 42. In other words, most of the insertion portion 42 is formed as a flexible part. The antibreak 44 is fixed to the proximal end of the flexible pipe 54. The support portion 46 is fixed to the proximal end of the antibreak 44. The cable 48 is fixed to the proximal end of the support portion 46. The proximal end of the cable 48 is connected to the controller 14.

The part of the insertion portion 42 of the endoscope 18 on the proximal side of the actuator 58 is formed as a crooked portion (first crooked portion) 66 provided with a shape having a bending habit. That is, the distal end 42a of the insertion portion 42 of the endoscope 18 includes a first area 43a on the distal side and a second area 43b on the proximal side across the crooked portion 66. An angle α of the first area 43a on the distal side to the second area 43b on the proximal side is preferably about 20° to about 70°. Between these angles, the angle α is particularly preferably about 45°. Due to the presence of the crooked portion 66, the distal end 52a of the insertion portion 42 of the endoscope 18 moves to draw a circular-ring orbit in response to the turning of the insertion portion 42 around a central axis C. The scanning endoscope 18 then actuates the actuator 58 to draw a spiral orbit. Thus, due to the rotation of the insertion portion 42 around the central axis C, an observable range of the subject can be wider than in a straight state (without the crooked portion 66). The crooked portion 66 is formed at the position of, for example, a distance (first distance) D1 from the distal face (distal end) 52a of the distal hard portion 52 toward the proximal side along the central axis C.

For example, the endoscope 18 has the upper side of the distal end 52a of the insertion portion 42 defined as an upward direction of the monitor 16 and has the lower side of the distal end 52a of the insertion portion 42 defined as a downward direction of the monitor 16. The left side and right side of the distal end 52a of the insertion portion 42 and the leftward direction and rightward direction of the monitor 16 are automatically defined when the upper side and lower side of the distal end 52a of the insertion portion 42 of the endoscope 18 and the upward direction and downward direction of the monitor 16 are defined. Although set as described above here, the upward and downward directions of the monitor can be set in any manner depending on the handle unit and the operator's preference.

As shown in FIG. 2A and FIG. 2B, the treatment instrument 20 includes a handle unit 102, the guide pipe 104, and a guide sheath 106. The handle unit 102 is grasped by the user and suitably operated. In this endoscopic treatment system 10, the insertion portion 42 of the endoscope 18, the guide sheath 106, and the guide pipe 104 are arranged in order from the inside of the central axis C to the outside.

The handle unit 102 includes a main body 112, guide rails 114, a first operation element 116 which moves the guide sheath 106, and a second operation element 118 which supports and moves the insertion portion 42 of the endoscope 18.

Figure 5A:
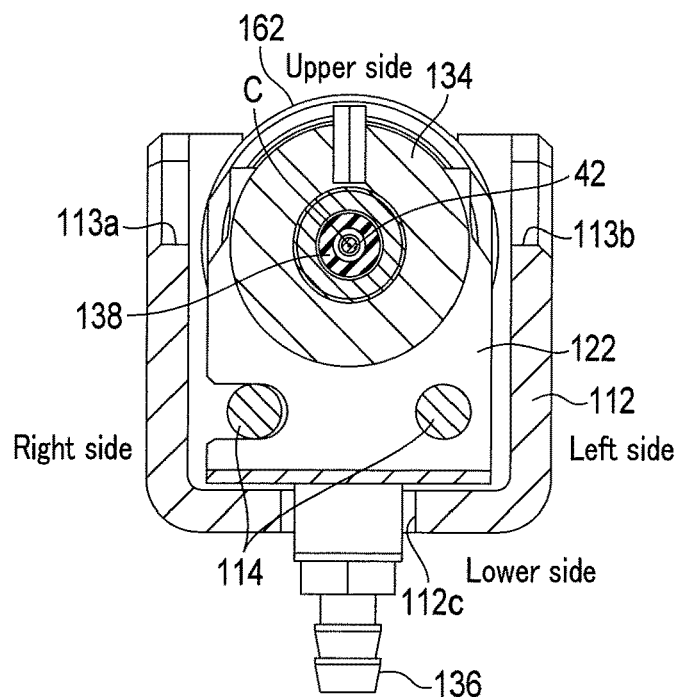
FIG. 5A is a schematic cross sectional view of the endoscopic treatment instrument unit along the arrow 5A-5A line in FIG. 2B.
Figure 5B:
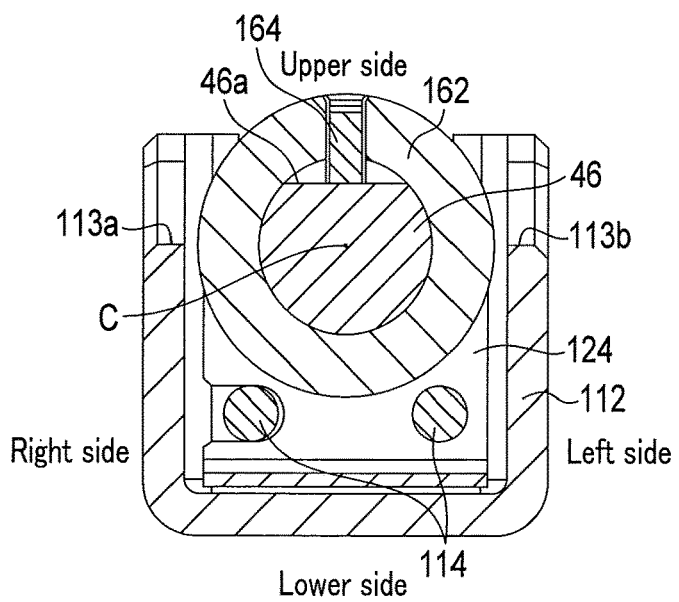
FIG. 5B is a schematic cross sectional view of the endoscopic treatment instrument unit along the arrow 5B-5B line in FIG. 2B.

As shown in FIG. 1A to FIG. 2B, the main body 112 defines a longitudinal axis L by its distal end 112a and proximal end 112b. As shown in FIG. 5A and FIG. 5B, the cross section of the main body 112 is substantially U-shaped. The upper side of the main body 112 is open. As shown in FIG. 2A and FIG. 2B, the guide rails 114 are fixed to the distal end 112a and the proximal end 112b of the main body 112, respectively.

The guide rail 114 is formed by a rod or a pipe which couples the distal end 112a and the proximal end 112b of the main body 112 straight to each other. The guide rail 114 is made of a rigid material such as stainless steel. One guide rail 114 is sufficient, but two (a pair of) guide rails 114 are preferably formed parallel to each other.

Figure 6A:
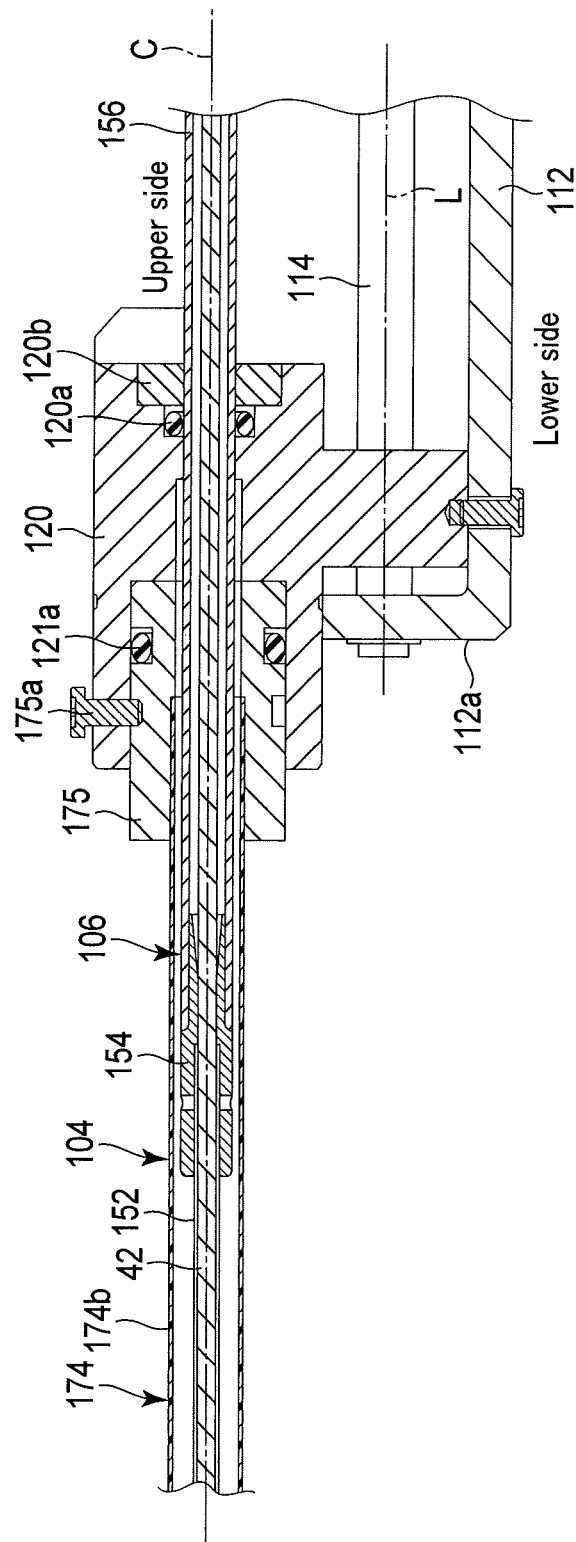
FIG. 6A is a schematic diagram showing, in an enlarged form, the endoscopic treatment instrument unit at a position indicated by the reference sign 6A in FIG. 2B in the vicinity of a connection pipe.

As shown in FIG. 2A, FIG. 2B, and FIG. 6A, a connection pipe 120 to which the proximal end of the guide pipe 104 is coupled is fixed to the distal end 112a of the main body 112. An O-ring 120a is provided between the inner circumferential surface of the connection pipe 120 and the outer circumferential surface of a later-described inner pipe 156 of the guide sheath 106. The O-ring 120a exerts suitable frictional force between the inner circumferential surface of the O-ring 120a and the outer circumferential surface of the inner pipe 156 of the guide sheath 106. Thus, the guide sheath 106 can be turned around the central axis C by the user operation and can be moved along the central axis C, but is inhibited from free movement. The O-ring 120a is prevented by a holding member 120b from coming off the proximal side of the connection pipe 120.

As shown in FIG. 2A, FIG. 2B, FIG. 5A, FIG. 5B, FIG. 6A, and FIG. 6B, first and second holders 122 and 124 which move along the guide rail 114 are provided between the distal end 112a and the proximal end 112b of the main body 112. The first holder 122 is close to the distal end 112a of the main body 112, and the second holder 124 is close to the proximal end 112b of the main body 112. The first and second holders 122 and 124 can come closer to and come in and out of contact with each other along the guide rail 114.

As shown in FIG. 5A and FIG. 6B, a T-shaped pipe 132 which is in communication with the space between the outer circumferential surface of the insertion portion 42 of the endoscope 18 and the inner circumferential surface of the guide sheath 106 is supported on the first holder 122. A first rotor 134 rotatable around the central axis C is provided at the distal end of the T-shaped pipe 132. The first holder 122, the T-shaped pipe 132, and the first rotor 134 constitute the first operation element 116. The first operation element 116 can move the guide sheath 106 in its axial direction relative to the guide pipe 104 and the insertion portion 42 and can also turn the guide sheath 106 around its axis. That is, the first operation element 116 can move the guide sheath 106 relative to the guide pipe 104 and the insertion portion 42.

A joint 136 which communicates with the central axis C of the T-shaped pipe 132 and the first rotor 134 through a pipeline 132a is connected to the T-shaped pipe 132. The joint 136 protrudes from an opening 112c of the main body 112 of the handle unit 102. The suction source 22, the liquid supply source 24, the change-over valve 28, and the on-off valve 30 are connected to the joint 136 as shown in FIG. 1A.

O-rings 138a and 138b are respectively disposed between the outer circumferential surface of the distal end of the T-shaped pipe 132 and the first rotor 134 and between the inner circumferential surface of the proximal end of the T-shaped pipe 132 and the outer circumferential surface of the insertion portion 42 of the endoscope 18. In particular, the O-ring 138b is prevented by a holding member 140 from coming off the proximal side of the T-shaped pipe 132. Thus, when a gas or a liquid is supplied from the joint 136, the gas or the liquid can be guided toward the distal side of the T-shaped pipe 132.

The O-ring 138b exerts suitable frictional force between its inner circumferential surface and the outer circumferential surface of the insertion portion 42 of the endoscope 18. Thus, the insertion portion 42 of the endoscope 18 can be turned around the central axis C by the user operation and can be moved along the central axis C, but is inhibited from free movement. Here, the frictional force between the inner circumferential surface of the O-ring 138b and the outer circumferential surface of the insertion portion 42 of the endoscope 18 is set to such a degree that the second operation element 118 does not unintentionally move in response to the movement of the first operation element 116 and the movement of the insertion portion 42.

The O-ring 138a exerts suitable frictional force between its outer circumferential surface and the first rotor 134. Thus, the first rotor 134 can be turned around the central axis C by the user operation and can be moved along the central axis C, but is inhibited from free movement.

Figure 7:
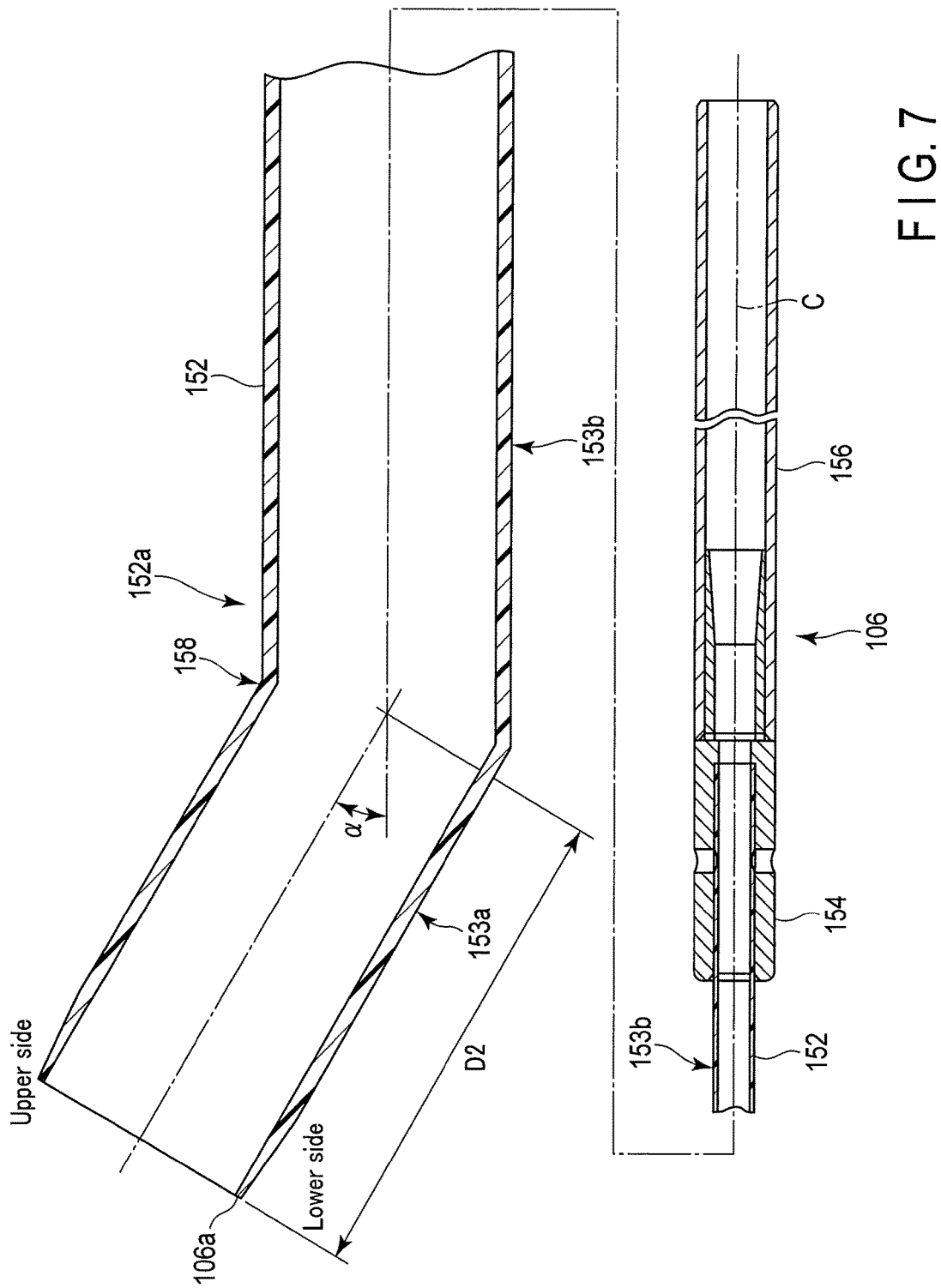
FIG. 7 is a schematic longitudinal sectional view showing a guide sheath of the treatment instrument unit according to the first embodiment.

Here, the guide sheath 106 shown in FIG. 7 has an inside diameter which allows the insertion portion 42 to be inserted therethrough so that the distal end 52a of the insertion portion 42 can protrude relative to its distal end 106a, and the guide sheath 106 is inserted through the guide pipe 104 so that its distal end 106a can protrude relative to the distal end 104a of the guide pipe 104.

As shown in FIG. 7, the guide sheath 106 includes a sheath main body 152, a sheath holder 154, and the inner pipe 156 from the distal side to the proximal side.

The sheath main body 152 is formed into a tubular shape by an elastically deformable resin material having a thickness of, for example, about 0.1 mm. The sheath main body 152 is filled with a meshed tube (not shown) called a braid. Thus, the sheath main body 152 according to this embodiment is sturdier than when simply made of a resin material. That is, the sheath main body 152 of the guide sheath 106 has a small thickness but has satisfactory rotation following properties around the central axis C and is easily bendable, and is unbreakably formed to ensure a hollow part therein. The sheath main body 152 is preferably formed to be more unbendable than the flexible pipe 54 of the insertion portion 42 of the endoscope 18 shown in FIG. 3. Thus, when the whole distal hard portion 52 of the insertion portion 42 and part of the flexible pipe 54 protrude from the distal end 106a of the sheath main body 152, the position of the distal hard portion 52 can be held in a desired state.

The sheath holder 154 shown in FIG. 6A and FIG. 7 is formed into a cylindrical shape by a rigid material such as stainless steel. The outer circumferential surface of the proximal end of the sheath main body 152 is fixed to the inner circumferential surface of the sheath holder 154 by, for example, bonding. The inner circumferential surface of the distal end of the inner pipe 156 made of a rigid material such as stainless steel is fixed to the outer circumferential surface of the sheath holder 154 by, for example, bonding. The proximal end of the inner pipe 156 is fixed to the inner circumferential surface of the first rotor 134 by, for example, bonding. Thus, the inner pipe 156, the sheath holder 154, and the sheath main body 152, that is, the guide sheath 106 move together with the movement of the first operation element 116.

More specifically, if the first operation element 116 is moved forward along the central axis C, the inner pipe 156, the sheath holder 154, and the sheath main body 152, that is, the guide sheath 106 moves forward along the central axis C. If the first operation element 116 is moved back along the central axis C, the inner pipe 156, the sheath holder 154, and the sheath main body 152, that is, the guide sheath 106 moves back along the central axis C. If the first operation element 116 is rotated or turned around the central axis C, the inner pipe 156, the sheath holder 154, and the sheath main body 152, that is, the guide sheath 106 rotate or turn around the central axis C in the same direction as the rotation or turning direction of the first operation element 116.

As shown in FIG. 7, a crooked portion 158 provided with a shape of a bending habit is formed at a position of the sheath main body 152 of the guide sheath 106 located a distance (second distance) D2 from the distal end 106a of the sheath main body 152 toward the proximal side. That is, a distal end 152a of the sheath main body 152 includes a first area 153a on the distal side and a second area 153b on the proximal side across the crooked portion (second crooked portion) 158. An angle β of the first area 153a on the distal side to the second area 153b on the proximal side is, for example, about 20° to about 70°, and is preferably about 45°. Due to the presence of this crooked portion 158, the distal end 106a of the guide sheath 106 moves to draw a circular-ring orbit in response to the turning of the guide sheath 106 around the central axis C. Thus, the range in which the distal end 106a of the sheath main body 152 can be directed to the affected part (treatment target) can be wider than in a straight state (without the crooked portion 158).

The distance D2 preferably corresponds to the distance D1 (see FIG. 3) from the distal end 52a of the distal hard portion 52 of the crooked portion 66 formed in the insertion portion 42 of the endoscope 18. That is, when the distal end 106a of the sheath main body 152 of the guide sheath 106 corresponds to the distal end of the insertion portion 42 of the endoscope 18 (the distal face 52a of the distal hard portion 52), the crooked portions 66 and 158 are located at the same position. The upper side and lower side of the distal end 106a of the sheath main body 152 of the guide sheath 106 respectively correspond to the upper side and lower side of the insertion portion 42 of the endoscope 18 shown in FIG. 3. Thus, when the distal end 106a of the sheath main body 152 of the guide sheath 106 corresponds to the distal end of the insertion portion 42 of the endoscope 18 (the distal face 52a of the distal hard portion 52) and when the upper sides and lower sides correspond to each other, the rotation following properties of the guide sheath 106 and the endoscope 18 in combination improve compared to the rotation following properties obtained when the guide sheath 106 and the endoscope 18 are independent. As a result, operability improves. However, the distance D1 and the distance D2 do not always need to correspond to each other. For example, if the distance D1> the distance D2, the distal end of the endoscope having a small outer shape protrudes when the crooked portions 66 and 158 correspond to each other, and entry into a thin path is easier. If the distance D2> the distance D1, the distal end of the endoscope is located farther than the distal end 106a of the guide sheath when the crooked portions 66 and 158 correspond to each other, and a field of view is easily ensured even if the device bumps into a tissue.

Each of the crooked portion (a shape of a bending tendency) 66 formed in the insertion portion 42 of the endoscope 18 and the crooked portion (a shape of a bending tendency) 158 formed in the guide sheath 106 is not exclusively disposed at one place.

As shown in FIG. 2A, FIG. 2B, and FIG. 5B, a second rotor 162 capable of rotating around the central axis C is provided in the second holder 124. The second rotor 162 supports the support portion 46 on the proximal side of the antibreak 44 of the insertion portion 42 of the endoscope 18.

Here, the cross section of the support portion 46 of the endoscope 18 is substantially D-shaped. That is, the support portion 46 has a plane 46a. The plane 46a of the support portion 46 is stopped from rotating relative to the second rotor 162 by a pin 164. Thus, if the second rotor 162 is turned around the central axis C, the support portion 46, the antibreak 44, and the insertion portion 42 of the endoscope 18 turn around the central axis C. The second holder 124 and the second rotor 162 form the second operation element 118. The second operation element 118 can move the insertion portion 42 in its axial direction relative to the guide pipe 104 and the guide sheath 106 and can turn the insertion portion 42 in its axial direction. That is, the second operation element 118 can move the insertion portion 42 relative to the guide pipe 104 and the guide sheath 106.

The guide pipe 104 can observe the distal side of the distal end 52a of the insertion portion 42 and the distal side of the distal end 104a by the observation optical system 64 through the distal end 104a. The guide pipe 104 allows the insertion portion 42 to be inserted therethrough so that the distal side of the distal end 52a of the insertion portion 42 can be observed by the observation optical system 64 while allowing the distal end 52a of the insertion portion 42 to protrude relative to the distal end 104a.

Figure 8A:
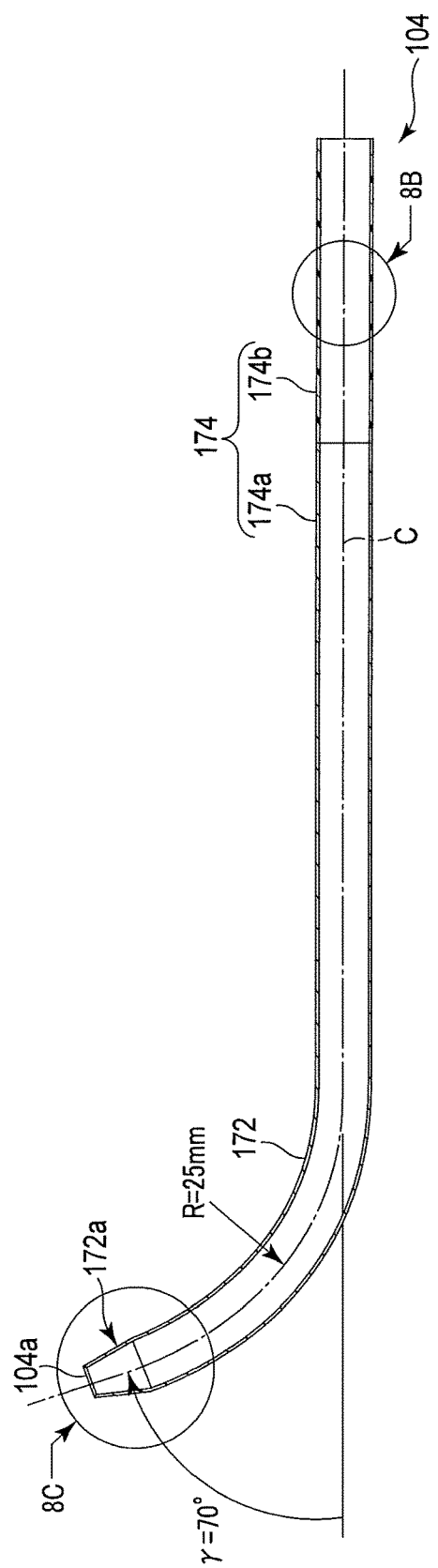
FIG. 8A is a schematic longitudinal sectional view showing a guide pipe of the treatment instrument unit of the treatment system according to the first embodiment.
Figure 8B:
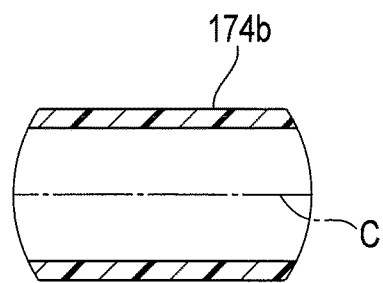
FIG. 8B is a schematic enlarged view showing an elastic portion of a straight pipe of the guide pipe indicated by the reference sign 8B in FIG. 8A.

As shown in FIG. 8A, the guide pipe 104 has a bent pipe 172 and a straight pipe 174 that are continuously formed. The guide pipe 104 has an inside diameter (e.g. about 1.5 to 3.0 mm) through which the insertion portion 42 of the endoscope 18 and the sheath main body 152 of the guide sheath 106 can be inserted. The bent pipe 172 is bent at an angle γ of, for example, about 70° to the straight pipe 174. The guide pipe 104 shown in FIG. 8A is used to treat, for example, the frontal sinus in the paranasal sinus.

Here, the inside diameter and bending radius R (e.g. about 5 to 25 mm) of the bent pipe 172 of the guide pipe 104 shown in FIG. 8A are set in consideration of a length (rigid length) from the distal face 52a of the distal hard portion 52 of the insertion portion 42 of the endoscope 18 to the proximal side along the central axis C when the sheath main body 152 of the guide sheath 106 is disposed on the outer circumference. Here, to perform an observation by the endoscope 18, the guide pipe 104 has its inside diameter larger than when a simple guide wire or light guide fiber is used. Moreover, the inside diameter of the straight pipe 174 in particular can be smaller than the inside diameter of the bent pipe 172, but is substantially the same inside diameter to more effectively perform suction performance.

A distal end 172a of the guide pipe 104 is tapered. Thus, the distal end 172a of the guide pipe 104 fits in the entrance of the paranasal sinus, and owing to the size of the entrance, the distal end 104a can be easily disposed on the far side from the near side of the entrance (opening) of the paranasal sinus. The distal end 104a of the guide pipe 104 is formed to have an inside diameter slightly larger than the outside diameter of the distal end 42a of the insertion portion 42 of the endoscope 18 so that the distal end 42a of the insertion portion 42 of the endoscope 18 can pass through the distal end 104a. This inside diameter is preferably is, for example, about 1.5 to 3.0 mm.

Therefore, the straight pipe 174 of the guide pipe 104 allows the guide sheath 106 to be moved while the insertion portion 42 is inserted through the guide sheath 106. The bent pipe 172 of the guide pipe 104 is located on the distal side of the straight pipe 174, and has an inside diameter and a bending radius that permit the distal hard portion 52 of the insertion portion 42 to protrude on the distal side through the distal end 104a of the guide pipe 104 while the insertion portion 42 is inserted through the guide sheath 106.

The straight pipe 174 of the guide pipe 104 is made of a combination of a rigid material such as stainless steel and a flexible material such as a silicone material. That is, the straight pipe 174 has a rigid portion 174a and an elastically deformable elastic portion 174b shown in FIG. 8B. That is, at least part of the straight pipe 174 is elastically deformable. Here, the part of the straight pipe 174 from the proximal end of the rigid portion 174a (the distal end of the elastic portion 174b) to the distal end of the bent pipe 172 is seamlessly and integrally formed by a stainless steel material. The elastic portion 174b may be formed at any position between the distal end and proximal end of the straight pipe 174. Owing to such an elastic portion 174b, if, for example, the distal end 172a of the bent pipe 172 or the distal end 104a abuts on a living tissue, the straight pipe 174 is elastically deformed in the elastic portion 174b. Thus, it is possible to prevent the guide pipe 104 from applying a load on the living tissue.

Similar advantageous effects can be obtained even if the straight pipe 174 is formed with suitable (given) flexibility as shown in FIG. 8E. However, the straight pipe 174 of the guide pipe 104 is preferably more high rigid than the guide sheath 106 and the insertion portion 42 of the endoscope 18. Thus, it is possible to guide the guide sheath 106 and the insertion portion 42 of the endoscope 18 which are inserted through the guide pipe 104. It is also preferable that in the guide pipe 104, not only the straight pipe 174 but also the bent pipe 172 is formed to be more high rigid than the guide sheath 106 and the insertion portion 42 of the endoscope 18 and the guide pipe 104 is made of a resin material which has suitable flexibility.

As shown in FIG. 6A, an adapter 175 is fixed to the proximal end of the elastic portion 174b of the straight pipe 174 of the guide pipe 104. The adapter 175 is fixed to the connection pipe 120 by a fixed element 175a such as a screw.

An O-ring 121a is provided between the connection pipe 120 and the adapter 175 of the guide pipe 104. Thus, the space between the guide pipe 104 and the adapter 175 is sealed. Therefore, the space between the inner circumferential surface of the guide pipe 104 and the adapter 175 can be airtight and/or liquidtight.

Figure 8C:
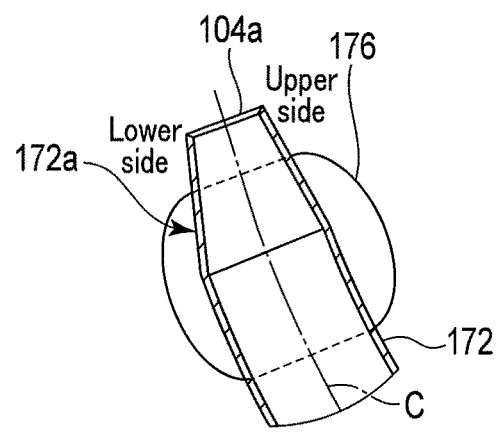
FIG. 8C is a schematic enlarged view showing the distal end of a bent pipe of the guide pipe indicated by the reference sign 8C in FIG. 8A.

The distal end 104a of the guide pipe 104 shown in FIG. 8C is formed into a rounded shape. Thus, applying a load on a mucous membrane in the nose is prevented.

As shown in FIG. 8C, a balloon 176 which can be elastically deformed into, for example, a ring shape is preferably disposed on the outer circumferential surface of the distal end 172a of the bent pipe 172. The balloon 176 is preferably inflated by air or a liquid sent via the joint 136, the outside of the guide sheath 106, and the inside or outside of the guide pipe 104. The balloon 176 is used to cause the distal end 104a of the guide pipe 104 to abut on and be supported on the vicinity of the entrance of the treatment target from the inside or outside of the paranasal sinus in accordance with the size of the opening of the paranasal sinus. The balloon 176 can prevent the distal end 172a of the guide pipe 104 from easily put into the slightly larger entrance of the paranasal sinus. The balloon 176 can be elastically deformed relative to the slightly larger entrance of the paranasal sinus and then held in the paranasal sinus, and prevent the distal end 104a of the guide pipe 104 from easily coming off the entrance of the paranasal sinus. It is possible to perform an observation or treatment in the paranasal sinus with the stable endoscope 18. That is, by inflating the balloon 176, the outer circumferential surface of the distal end 172a of the guide pipe 104 can be held to the entrance of the paranasal sinus around the opening of the paranasal sinus. Thus, by inflating the balloon 176, it is possible to prevent the distal end 172a of the guide pipe 104 from being unstable and displaced relative to the entrance of the paranasal sinus and then damaging the tissue.

Figure 8D:
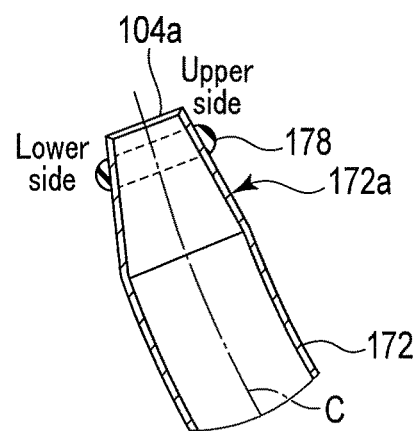
FIG. 8D is a schematic enlarged view showing the distal end of the bent pipe of the guide pipe indicated by the reference sign 8C in FIG. 8A in a modification of FIG. 8C.

As shown in FIG. 8D, it is also preferable to use a flexible ring 178 such as a rubber material instead of the balloon 176. As the balloon 176 shown in FIG. 8C, the ring 178 can be used to prevent the distal end 172a of the guide pipe 104 from being easily put into the slightly larger entrance of the paranasal sinus. The ring 178 can also be elastically deformed relative to the slightly larger entrance of the paranasal sinus and then held therein, and prevent the distal end 104a of the guide pipe 104 from coming off the entrance of the paranasal sinus, and prevent the guide pipe 104 from overly entering the paranasal sinus so that the position of the distal end 52a of the insertion portion 42 of the endoscope 18 may be unstable.

Here, for the simplification of explanation, the bending direction of the bent pipe 172 relative to the straight pipe 174 in the guide pipe 104 is defined on the upper side (see FIG. 1B) relative to the main body 112 of the handle unit 102.

Although the bending direction of the bent pipe 172 relative to the straight pipe 174 in the guide pipe 104 described in this embodiment is upward (the opening direction of the main body 112 of the handle unit 102), the bending direction can be set suitably to the user's preference.

Figure 9:
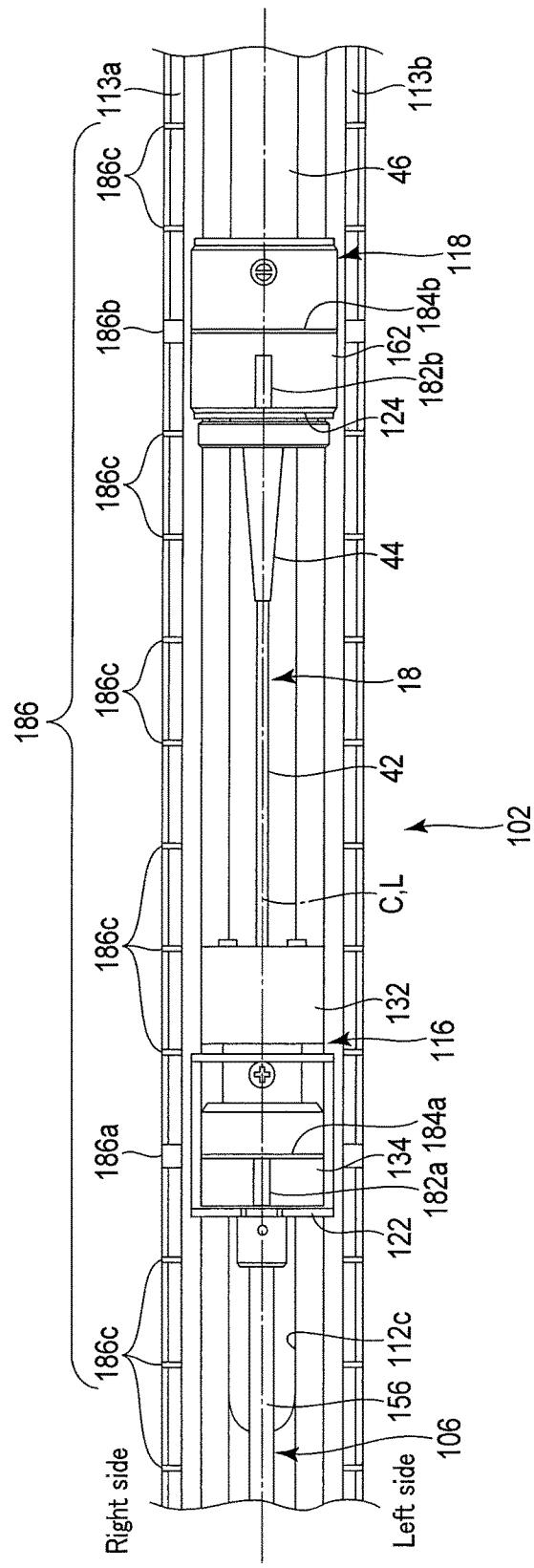
FIG. 9 is a schematic top view showing how indexes are formed in a handle unit of the endoscopic treatment instrument unit of the treatment system from the direction of an arrow 2A in FIG. 1A.

As shown in FIG. 9, a rotation direction index 182a is attached to the outer circumferential surface of the first rotor 134 in the first operation element 116. The rotation direction index 182a is used to recognize the bending direction of the first area 153a relative to the second area 153b, that is, the direction of the distal end 106a of the guide sheath 106 resulting from the crooked portion 158 of the sheath main body 152 of the guide sheath 106. When the rotation direction index 182a is located immediately above the main body 112 of the handle unit 102 as shows in FIG. 9, the bending direction of the bent pipe 172 of the guide pipe 104 corresponds to the bending direction of the first area 153a of the guide sheath 106.

The user can then recognize the direction of the distal end 106a of the guide sheath 106 by recognizing the position of the index 182a.

A rotation direction index 182b is attached to the outer circumferential surface of the second rotor 162 in the second operation element 118. The rotation direction index 182b is used to recognize the bending direction of the first area 43a relative to the second area 43b, that is, the direction of the distal end 52a of the insertion portion 42 resulting from the crooked portion 66 of the insertion portion 42 of the endoscope 18. When the rotation direction index 182b is located immediately above the main body 112 of the handle unit 102 as shows in FIG. 9, the bending direction of the bent pipe 172 of the guide pipe 104 corresponds to the bending direction of the first area 43a at the distal end 42a of the insertion portion 42 of the endoscope 18.

The user can then recognize the direction of the distal end 52a of the insertion portion 42 by recognizing the position of the index 182b.

In FIG. 9, the rotation direction indexes 182a and 182b are drawn as parallel segments having proper lengths parallel to the central axis C and the longitudinal axis L. It will be appreciated that instead of the segments, marks to be recognized by the user or click sensations during operation may be used as the rotation direction indexes 182a and 182b.

An annular index 184a that intersects at right angles with the central axis C is attached to the outer circumferential surface of the first rotor 134 in the first operation element 116. An annular index 184b that intersects at right angles with the central axis C is attached to the outer circumferential surface of the second rotor 162 in the second operation element 118.

The annular indexes 184a and 184b in FIG. 9 do not always need to be annularly attached, and it is also preferable that marks are attached at proper intervals.

Axial direction indexes 186 which indicate a positional relation between the first operation element 116 and the main body 112 and also indicate a positional relation between the second operation element 118 and the main body 112 are attached to a right edge 113a and a left edge 113b of the main body 112 of the handle unit 102. The axial direction indexes 186 are attached parallel to the longitudinal axis L at regular intervals. The axial direction indexes 186 have first and second main indexes 186a and 186b, and subindexes 186c. Here, in FIG. 9, the first and second main indexes 186a and 186b are drawn thicker than the subindexes 186c. The first main index 186a, the second main index 186b, and the subindexes 186c can be variously modified, for example, can be indicated in different colors distinguishably from one another.

The first main index 186a is located adjacent to the annular index 184a of the first operation element 116 when the distal end 104a of the guide pipe 104 corresponds to the distal end 106a of the guide sheath 106. The second main index 186b is located adjacent to the annular index 184b of the second operation element 118 when the distal end 104a of the guide pipe 104 corresponds to the distal end of the insertion portion 42 of the endoscope 18. Thus, the first main index 186a defines a neutral position of the first operation element 116, and the second main index 186b defines a neutral position of the second operation element 118.

The subindexes 186c are attached at regular intervals not only between the first and second main indexes 186a and 186b but also from the first main index 186a to the distal end 112a of the main body 112 of the handle unit 102 and from the second main index 186b to the proximal end 112b of the main body 112 of the handle unit 102. The interval between the subindexes 186c can be suitably set, for example, to 10 mm.

Therefore, when the first operation element 116 is moved relative to the main body 112 of the handle unit 102, the user can easily recognize the position of the distal end 106a of the guide sheath 106 relative to the distal end 104a of the guide pipe 104 and the direction in which the distal end 106a is bent by the crooked portion 158. When the second operation element 118 is moved relative to the main body 112 of the handle unit 102, the user can also easily recognize the position of the distal end 52a of the insertion portion 42 of the endoscope 18 relative to the distal end 104a of the guide pipe 104 and the direction in which the distal end 52a is bent by the crooked portion 66. Further, by recognizing the positional relation between the first operation element 116 and the second operation element 118, the user can easily recognize the position of the distal end 52a of the insertion portion 42 of the endoscope 18 relative to the distal end 106a of the guide sheath 106 and the direction in which the distal end 52a is bent by the crooked portion 66.

Although the axial direction indexes 186 are attached to both of the pair of edges 113a and 113b in the example described here, it is also preferable that the axial direction indexes 186 are attached to only one of the pair of edges 113a and 113b.

In has been explained here that the axial direction indexes 186 are attached to the pair of edges 113a and 113b. Although not shown, it is also preferable that the indexes 186 are attached to not only to the edges 113a and 113b but also to the side surface of the main body 112 of the handle unit 102 that continues to the edges 113a and 113b.

It is also preferable that the indexes 182a, 182b, 184a, 184b, and 186 are formed to be visually recognizable and to be recognizable when touched by the user.

It is preferable that an interlock mechanism (switch mechanism) 190 which maintains the positional relation between the first operation element 116 and the second operation element 118 is disposed in the handle unit 102.

The interlock mechanism 190 can be brought into an interlocked state to move the first operation element 116 and the second operation element 118 together, and a non-interlocked state to separately and independently move the first operation element 116 and the second operation element 118. Thus, the interlock mechanism 190 functions as a switch unit which can switch to the interlocked state and the non-interlocked state.

As an example of the interlock mechanism 190, a known wire type rim brake can be disposed in the first rotor 134, for example, as shows in FIG. 10. That is, the interlock mechanism 190 is provided in the first rotor 134.

The interlock mechanism 190 includes a pair of movable bodies 192a and 192b facing across the insertion portion 42, brake shoes 194a and 194b provided in the movable bodies 192a and 192b, a traction wire 196 having an interlocking body 196a coupled to the movable bodies 192a and 192b, and a base 198 having a press pad 198a coupled to the traction wire 196. The pair of movable bodies 192a and 192b are turnably supported on the first rotor 134 by support shafts 193a and 193b, respectively. The press pad 198a functions in the same manner as a break lever. If the press pad 198a is pressed against the base 198, the traction wire 196 is pulled. If the traction wire 196 is pulled toward the press pad 198a, the movable bodies 192a and 192b turn around the axes of the support shafts 193a and 193b, and then the brake shoes 194a and 194b come closer to each other. Thus, the brake shoes 194a and 194b hold the outer circumferential surface of the insertion portion 42. On the other hand, if the press pad 198a is unpressed, the brake shoes 194a and 194b separate from each other and release the outer circumferential surface of the insertion portion 42. Thus, the interlock mechanism 190 can actuate the first operation element 116 and the second operation element 118 independently of or dependently on each other.

Therefore, if, for example, the first operation element 116 is moved forward along the central axis C in a situation in which the interlock mechanism 190 is switched to the interlocked state (the press pad 198a is in the pressed state), the interlock mechanism 190 interlocks to move the second operation element 118 the same distance forward. If the first operation element 116 is moved back along the central axis C, the interlock mechanism 190 interlocks to move the second operation element 118 the same distance back. Similarly, if, for example, the first operation element 116 is turned around the central axis C in a situation in which the interlock mechanism 190 is switched to the interlocked state, the interlock mechanism 190 interlocks to turn the second operation element 118 the same angle. When the second operation element 118 is operated, the first operation element 116 operates together. On the other hand, in a situation in which the interlock mechanism 190 is switched to the noninterlocked state (the press pad 198a is in the released state), the interlock mechanism 190 independently operates the first operation element 116 and the second operation element 118.

For example, if the interlock mechanism 190 is kept switched to the interlocked state in a situation in which the first and second operation elements 116 and 118 are disposed at the positions shown in FIG. 9 relative to the main body 112 of the handle unit 102, the distal end 52a of the insertion portion 42 and the distal end 106a of the guide sheath 106 move together.

Next, the function of the treatment system 10 according to this embodiment is described with reference to FIG. 11 to FIG. 14.

By properly moving the first and second operation elements 116 and 118, the user can properly observe the condition outside the treatment instrument 20 while observing the distal end 104a of the guide pipe 104 and the distal end 106a of the guide sheath 106 by the observation optical system 64 of the insertion portion 42 of the endoscope 18.

By properly moving the first and second operation elements 116 and 118, the user can cause the distal end 52a of the insertion portion 42 to be flush with or protrude from the distal end 104a of the guide pipe 104 and the distal end 106a of the guide sheath 106. In a situation in which the distal end 52a of the insertion portion 42 of the endoscope 18 is protruding out of the treatment instrument 20, the condition outside the treatment instrument 20 can be properly observed by the observation optical system 64 of the insertion portion 42 of the endoscope 18. In this case, blocking of the field of views for the distal end 104a of the guide pipe 104 and the distal end 106a of the guide sheath 106 is prevented, so that a wider range can be observed.

An example of treating, for example, the frontal sinus in the paranasal sinus using the treatment system 10 is described below. That is, a series of procedures using the treatment system 10 are performed as below.

(Step 0) The treatment instrument unit 12 of the treatment system 10 is prepared as below.

The insertion portion 42 of the endoscope 18 is inserted through the guide pipe 104 and the guide sheath 106 of the treatment instrument unit 12 to form the treatment instrument unit 12.

As shown in FIG. 9, the annular index 184a of the first operation element 116 is placed adjacent to the first main index 186a formed on the edges 113a and 113b of the main body 112 of the handle unit 102. The annular index 184b of the second operation element 118 is placed adjacent to the second main index 186b. In this instance, the distal end 104a of the guide pipe 104, the distal end 106a of the guide sheath 106, and the distal end 52a of the insertion portion 42 of the endoscope 18 are at the same position. The crooked portion 158 of the guide sheath 106 and the crooked portion 66 of the insertion portion 42 of the endoscope 18 are at the same position.

The rotation direction index 182a of the first operation element 116 is disposed on the upper side of the main body 112 of the handle unit 102. In this instance, the bending direction of the bent pipe 172 relative to the straight pipe 174 of the guide pipe 104 corresponds to the bending direction of the first area 153a relative to the second area 153b of the guide sheath 106. The rotation direction index 182b of the second operation element 118 is disposed on the upper side of the handle unit 102. In this instance, the bending direction of the bent pipe 172 relative to the straight pipe 174 of the guide pipe 104 corresponds to the bending direction of the first area 43a relative to the second area 43b of the insertion portion 42 of the endoscope 18. Further, the bending direction of the first area 153a by the crooked portion 158 of the guide sheath 106 corresponds to the bending direction of the first area 43a by the crooked portion 66 of the insertion portion 42 of the endoscope 18.

Thus, the first operation element 116 and the second operation element 118 are disposed at neutral positions relative to the main body 112 of the handle unit 102.

Owing to friction between the outer circumferential surface of the guide sheath 106 and the O-ring 120a disposed in the connection pipe 120 and friction between the O-ring 138a disposed in the first operation element 116 and the first rotor 134, the first operation element 116 is inhibited from unintentionally turning by, for example, gravity and unintentionally moving along the central axis C. Similarly, owing to friction between the outer circumferential surface of the insertion portion 42 of the endoscope 18 and the O-ring 138b disposed in the first operation element 116, the second operation element 118 is inhibited from unintentionally turning by, for example, gravity and unintentionally moving along the central axis C. In this instance, frictional force between the inner circumferential surface of the O-ring 138b and the outer circumferential surface of the insertion portion 42 of the endoscope 18 is set so to such a degree that the first operation element 116 and the second operation element 118 independently move.

The press pad 198a of the interlock mechanism 190 is released. Thus, the first operation element 116 and the second operation element 118 independently operate.

(Step 1) The distal end 104a of the guide pipe 104 and the distal end 106a of the guide sheath 106 of the treatment instrument unit 12 of the treatment system 10, and the distal end 52a of the insertion portion 42 of the endoscope 18 are inserted to the entrance (opening) of the paranasal sinus which is a treatment target from an external nostril.

The user (doctor) grasps the handle unit 102. The user guides the distal end 104a of the guide pipe 104 of the treatment instrument unit 12 to the entrance of the frontal sinus in the paranasal sinus from, for example, the external nostril while maintaining the condition described above in (Step 0).

In this instance, the user properly moves the handle unit 102 while visually recognizing the monitor 16 which displays the images observed by the endoscope 18. The user disposes the distal end 104a of the guide pipe 104 in the vicinity of the entrance of the frontal sinus in the paranasal sinus from the external nostril. A middle nasal concha and a middle meatus are recognized on the monitor 16. A semilunar hiatus is then recognized. The entrance of the frontal sinus is then recognized above the semilunar hiatus.

When the distal end 52a of the insertion portion 42 of the endoscope 18 has come to a dead end, an observation image showing the color of a mucous membrane is displayed on the entire monitor 16. On the other hand, when there is an insertion path ahead of the distal end 52a of the insertion portion 42 of the endoscope 18, not only the mucous membrane but also passage through a narrowed area is displayed on the entire monitor 16.

A case in which there is an insertion path but the insertion path is narrow is described as a first condition.

Figure 11:
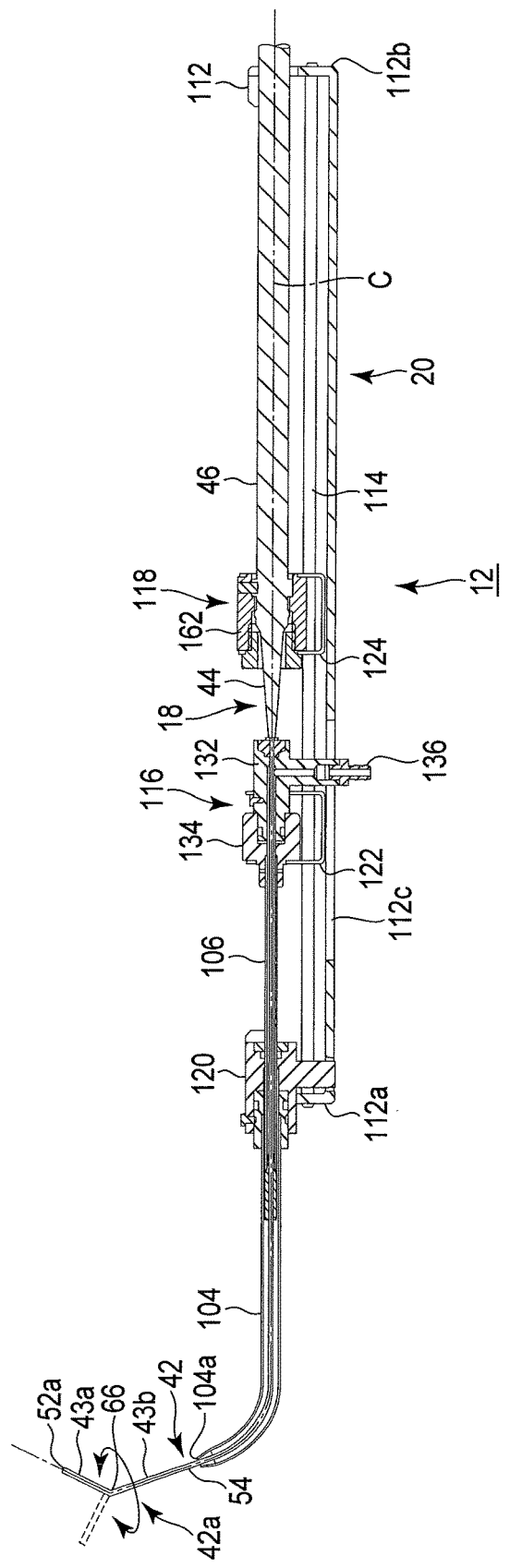
FIG. 11 is a schematic longitudinal sectional view of the endoscopic treatment instrument unit showing how the distal end of an insertion portion of the endoscope including a crooked portion is protruded relative to the distal end of the guide pipe of the treatment instrument unit of the treatment system according to the first embodiment, and the distal end of the insertion portion of the endoscope including the crooked portion is turnable on the crooked portion.
Figure 12:
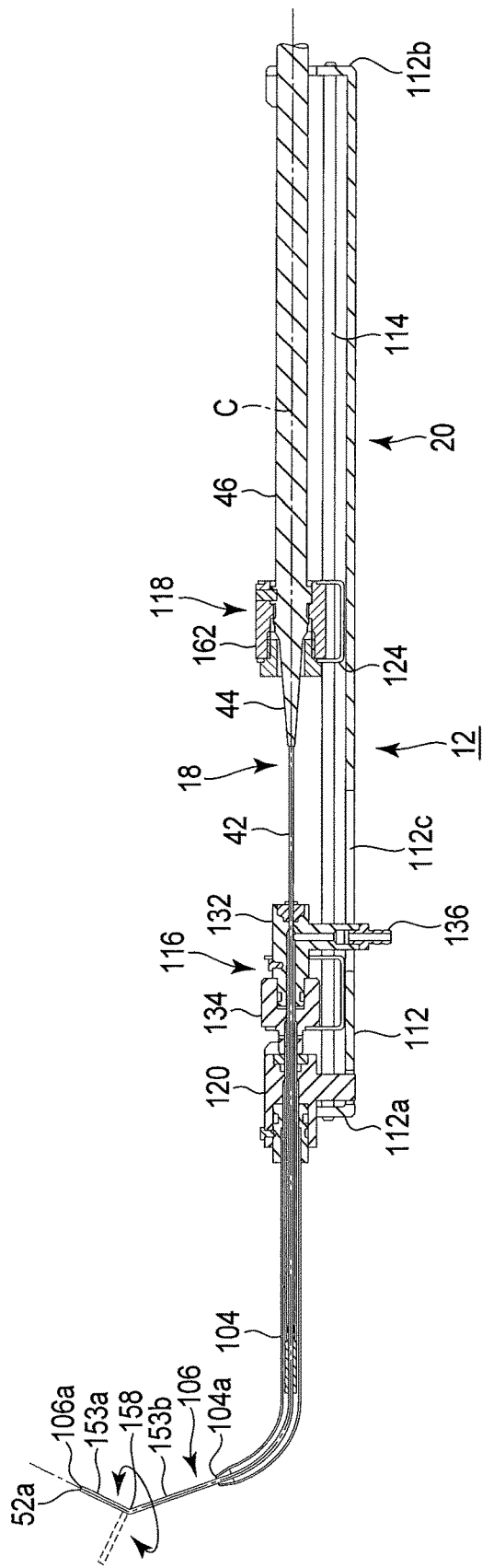
FIG. 12 is a schematic longitudinal sectional view of the endoscopic treatment instrument unit showing how the distal end of the guide sheath including the crooked portion and the distal end of the insertion portion of the endoscope including the crooked portion are protruded relative to the distal end of the guide pipe of the treatment instrument unit of the treatment system according to the first embodiment, and how the distal end of the guide sheath is aligned with the distal end of the insertion portion of the endoscope, the crooked portion of the guide sheath is aligned with the crooked portion of the insertion portion of the endoscope, and the distal end of the guide sheath including the crooked portion and the distal end of the insertion portion of the endoscope including the crooked portion are turnable on the crooked portion of the guide sheath.

When the user is visually recognizing an observation image of the endoscope 18 on the monitor 16, the user may recognize a narrow insertion path. As shown in FIG. 11, the second operation element 118 is moved closer to the first operation element 116 from the neutral position. The distal end 52a of the insertion portion 42 of the endoscope 18 is protruded to the distal end 104a of the guide pipe 104 and the distal end 106a of the guide sheath 106. In this instance, the user can observe the distal side of the distal end 52a of the insertion portion 42 by the observation optical system 64 while the distal end 52a of the insertion portion 42 is protruded to the distal end 104a of the guide pipe 104. The user then moves the second operation element 118 while observing the monitor 16 which displays the observation image of the endoscope 18. In this instance, the bending habit of the distal end 42a of the insertion portion 42 resulting from the crooked portion 66 is used to pass the distal end 52a of the insertion portion 42 through the narrow path. After the distal end 52a of the insertion portion 42 has passed through the narrow path or as the distal end 52a of the insertion portion 42 passes through the narrow path, the first operation element 116 is moved toward the distal end 112a of the main body 112 of the handle unit 102 as shown in FIG. 12. In this instance, the first operation element 116 may be moved while the second operation element 118 is being moved. The first operation element 116 is moved away from the second operation element 118, and the distal end 106a of the guide sheath 106 is moved closer to the distal end 52a of the insertion portion 42. In this instance, it is preferable that the circumferential positions and axial positions of the distal end 52a of the insertion portion 42 and the distal end 106a of the guide sheath 106 correspond to each other.

The distal end 106a of the guide sheath 106 and the distal end 52a of the insertion portion 42 are then inserted into the paranasal sinus through the entrance of the paranasal sinus. The user then properly moves the main body 112 while properly operating the first operation element 116 relative to the main body 112 of the handle unit 102. In this instance, the distal end 104a of the guide pipe 104 is moved along the insertion direction of the guide sheath 106 so that the condition in which the distal end 106a of the guide sheath 106 is disposed inside the paranasal sinus is maintained. Thus, the distal end 104a of the guide pipe 104 is disposed at the entrance of the frontal sinus in the paranasal sinus.

A case in which the insertion path is sufficient to pass both the distal end 52a of the insertion portion 42 and the distal end 106a of the guide sheath 106 is described as a second condition.

When the insertion path is sufficient to pass both the distal end 52a of the insertion portion 42 and the distal end 106a of the guide sheath 106, the guide sheath 106 and the insertion portion 42 of the endoscope 18 are protruded to the distal end 104a of the guide pipe 104. In this case, it is preferable that the first operation element 116 and the second operation element 118 are operated while the press pad 198a of the interlock mechanism 190 is pressed to interlock the first and second operation elements 116 and 118. That is, the first operation element 116 and the second operation element 118 are moved toward the distal end 112a of the main body 112 of the handle unit 102 so that the positional relation between the first operation element 116 and the second operation element 118 is maintained. In this instance, the user can observe the distal side of the distal end 52a of the insertion portion 42 by the observation optical system 64 while the distal end 52a of the insertion portion 42 is substantially flush with the distal end 104a of the guide pipe 104.

The distal end 106a of the guide sheath 106 and the distal end 52a of the insertion portion 42 are then inserted into the paranasal sinus through the entrance of the paranasal sinus. The user then properly moves the main body 112 while properly operating the first operation element 116 relative to the main body 112 of the handle unit 102. In this instance, the distal end 104a of the guide pipe 104 is moved along the insertion direction of the guide sheath 106 so that the condition in which the distal end 106a of the guide sheath 106 is disposed inside the paranasal sinus is maintained. Thus, the distal end 104a of the guide pipe 104 is disposed at the entrance of the frontal sinus in the paranasal sinus. The press pad 198a of the interlock mechanism 190 is then released.

A case in which viscous matter overly adheres to the insertion path is described as a third condition.

Figure 13:
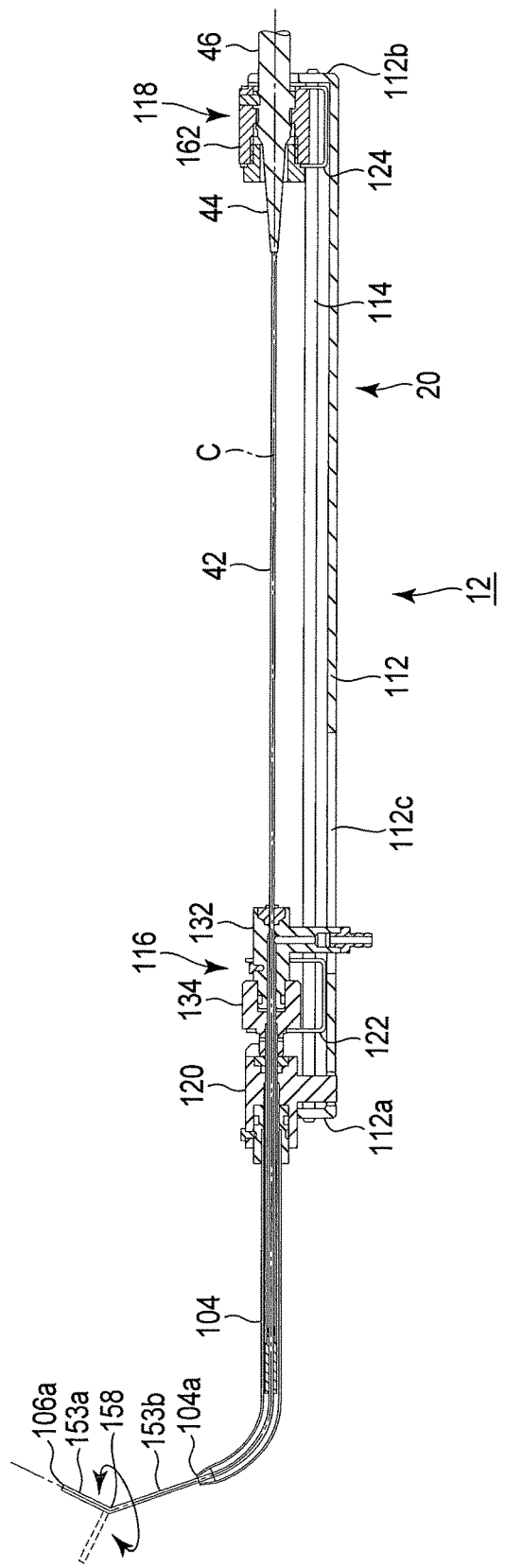
FIG. 13 is a schematic longitudinal sectional view of the endoscopic treatment instrument unit showing how the distal end of the guide sheath including the crooked portion is protruded relative to the distal end of the guide pipe of the treatment instrument unit of the treatment system according to the first embodiment, and how the insertion portion of the endoscope is disposed on the most proximal side in the guide pipe, and the distal end of the guide sheath including the crooked portion is turnable on the crooked portion of the guide sheath.

When it is recognized from the observation image of the endoscope 18 that viscous matter overly adheres to the insertion path, the distal end 106a of the guide sheath 106 is moved to the position close to the viscous matter while the observation image is being observed. That is, the first operation element 116 is moved toward the distal end 112a of the main body 112 of the handle unit 102. In this instance, the second operation element 118 is moved as required so that the viscous matter can be observed by the endoscope 18. In this instance, the user can observe the distal side of the distal end 52a of the insertion portion 42 by the observation optical system 64 through the distal end 106a of the guide sheath 106. After the end of the observation, the second operation element 118 is moved toward the proximal end 112b of the main body 112 of the handle unit 102 as shown in FIG. 13 while the position of the first operation element 116 is maintained. The suction source 22 shown in FIG. 1 is then actuated to suck the viscous matter from the distal end 106a of the guide sheath 106 through the space between the inner circumferential surface of the guide sheath 106 and the outer circumferential surface of the insertion portion 42. After the operation of the suction source 22 is stopped, the second operation element 118 is moved closer to the first operation element 116 as shown in FIG. 12 to align the distal end 52a of the insertion portion 42 with the distal end 106a of the guide sheath 106.

When the suction of the viscous matter is difficult, the second operation element 118 may be retreated to the proximal side, the inner bore of the guide pipe 104 may be released, and suction may be performed.

While the crooked portion 66 of the insertion portion 42 is disposed in the range of the distal end 152a (e.g. the first area 153a) of the guide sheath 106, the first area 153a of the guide sheath 106 will maintain its shape. That is, the first area 153a of the guide sheath 106 resists the bending habit of the crooked portion 66 of the insertion portion 42.

The insertion path is then confirmed, and the first and second operation elements 116 and 118 are properly operated as in the first condition and the second condition to insert the distal end 106a of the guide sheath 106 and the distal end 52a of the insertion portion 42 into the paranasal sinus. The user then properly moves the main body 112 while properly operating the first operation element 116 relative to the main body 112 of the handle unit 102. In this instance, the distal end 104a of the guide pipe 104 is moved along the insertion direction of the guide sheath 106 so that the condition in which the distal end 106a of the guide sheath 106 is disposed inside the paranasal sinus is maintained. Thus, the distal end 104a of the guide pipe 104 is disposed at the entrance of the frontal sinus in the paranasal sinus.

A condition in which the crooked portion 158 of the guide sheath 106 and the crooked portion 66 of the insertion portion 42 of the endoscope 18 are protruded relative to the distal end 104a of the guide pipe 104 may be set as a neutral condition. In this instance as well, the distal end 52a of the insertion portion 42 and the distal end 106a of the guide sheath 106 are disposed in the paranasal sinus as in the first to third conditions.

For example, when the distal end 104a of the guide pipe 104 of the treatment instrument unit 12 is disposed in the opening of the frontal sinus, there may be more than one entrance. In this case, the distal end 104a of the guide pipe 104 of the treatment instrument unit 12 is disposed at each entrance, the sinus on its far side is observed by the endoscope 18, and whether the sinus is the frontal sinus is judged. To select an insertion path, the handle unit 102 can be moved to select an insertion path to insert the guide sheath 106 and the distal end 52a of the insertion portion 42 of the endoscope 18.

It is also possible to judge whether the distal end 52a of the insertion portion 42 of the endoscope 18 can access a desired paranasal sinus if the operation room is darkened and an observation is performed and if the user visually recognizes, from the outside of the body, illumination light of the endoscope 18 which transmits bone and skin.

A magnetic or optical navigation system may be used in addition to this treatment system 10 to assist in selecting a path to insert the guide pipe 104 and the insertion portion 42 of the endoscope 18 into the paranasal sinus.

The user can observe the path from the external nostril to the entrance of the frontal sinus in detail by visually recognizing the monitor 16. In this instance, the part which the distal end 104a of the guide pipe 104 is facing is displayed on the monitor 16, so that it is possible to find the entrance of the frontal sinus from the semilunar hiatus and guide the distal end 104a of the guide pipe 104 to the entrance of the frontal sinus by the endoscope 18 by properly moving the distal end 104a of the guide pipe 104.

In this instance, even if the insertion path from the external nostril to the frontal sinus is unintentionally pressed by the bent pipe 172 of the guide pipe 104, it is possible to prevent great force from being applied to the insertion path owing to the elastic deformation of the elastic portion 174b.

The user holds the handle unit 102 without moving the distal end 104a of the guide pipe 104 to maintain the positional relation between the distal end 104a of the guide pipe 104 and the entrance of the frontal sinus in the paranasal sinus. The user inflates the balloon 176 (see FIG. 8C) disposed on the outer circumferential surface of the distal end 172a of the guide pipe 104 to prevent further insertion into the entrance of the frontal sinus in the paranasal sinus. When the opening is larger than the outside diameter of the guide pipe 104, the guide pipe 104 is put into the entrance of the frontal sinus, the balloon 176 is inflated at the place where a sufficient space can be secured, and the removal of the guide pipe 104 from the frontal sinus is prevented.

In contrast, when the insertion path is narrow and the distal end 52a of the insertion portion 42 of the endoscope 18 can not pass therethrough, the guide wire may move ahead or the path may be extended by the balloon 176 to attempt the insertion into the paranasal sinus.

Thus, the distal end 172a of the guide pipe 104 is disposed at the entrance of the frontal sinus in the paranasal sinus, so that the distal end 52a of the insertion portion 42 of the endoscope 18 and/or the distal end 106a of the guide sheath 106 can access the inside of the paranasal sinus.

(Step 2) The observation image of the endoscope 18 is then used to diagnose the inside of the paranasal sinus.

The distal end 172a of the guide pipe 104 is disposed at the entrance of the frontal sinus in the paranasal sinus. As shown in FIG. 2B, the distal end 106a of the guide sheath 106 and the distal end 52a of the insertion portion 42 of the endoscope 18 are located at the distal end 104a of the guide pipe 104. That is, the first and second operation elements 116 and 118 are disposed at the neutral positions. As shown in FIG. 12, the distal end 106a of the guide sheath 106 and the distal end 52a of the insertion portion 42 of the endoscope 18 are protruded from the distal end 104a of the guide pipe 104. In this instance, the distal end 106a of the guide sheath 106 and the distal end 52a of the insertion portion 42 of the endoscope 18 are located in the paranasal sinus.

In this condition, the second operation element 118 is moved to move the distal end 52a of the insertion portion 42 of the endoscope 18 to confirm the condition in the paranasal sinus, for example, whether the viscous matter is retained, the condition of the surface of the mucous membrane, the color and condition of mucus, and the condition of the mucous membrane by observing the monitor 16.

In this instance, as shown in FIG. 13 and FIG. 14, the second operation element 118 is moved closer to the first operation element 116, and the distal end 52a of the insertion portion 42 of the endoscope 18 is protruded relative to the distal end 106a of the guide sheath 106. The sheath main body 152 of the guide sheath 106 is more persevering and more unbendable than the insertion portion 42 of the endoscope 18. Thus, when the crooked portion 66 of the insertion portion 42 of the endoscope 18 is located between the distal end 106a of the guide sheath 106 and the crooked portion 158, the first area 153a of the guide sheath 106 maintains its substantially straight state ignoring the presence of the crooked portion 66 of the insertion portion 42 of the endoscope 18. On the other hand, the insertion portion 42 of the endoscope 18 is bent under the influence of the crooked portion 158 of the guide sheath 106. Thus, if the first operation element 116 and the second operation element 118 are simultaneously turned in the same direction around the central axis C, the distal end 52a of the insertion portion 42 moves to draw a circular-arc orbit on the crooked portion 158 of the guide sheath 106.

Even if the second operation element 118 alone is turned in a direction around the central axis C in this case, the distal end 52a of the insertion portion 42 hardly moves its position. Naturally, the image displayed on the monitor 16 turns.

The second operation element 118 is further moved closer to the first operation element 116, and the crooked portion 66 of the insertion portion 42 of the endoscope 18 is protruded relative to the distal end 106a of the guide sheath 106. In this condition, the second operation element 118 is turned around the central axis C. Thus, the distal end 52a of the insertion portion 42 moves to draw a circular-arc orbit on the crooked portion 66 of the insertion portion 42 of the endoscope 18. If the first operation element 116 and the second operation element 118 are simultaneously turned in the same direction around the central axis C, the distal end 52a of the insertion portion 42 moves to draw a circular-arc orbit on the crooked portion 158 of the guide sheath 106.

Naturally, while the crooked portion 158 of the guide sheath 106 is retracted in the guide pipe 104, the crooked portion 66 of the insertion portion 42 of the endoscope 18 may be protruded relative to the distal end 104a of the guide pipe 104 so that the distal end 52a of the insertion portion 42 will move to draw a circular-arc orbit on the crooked portion 66 of the insertion portion 42.

Thus, it is possible to adjust the position of the circular-arc orbit of the distal end 52a of the insertion portion 42 of the endoscope 18 by properly adjusting the positions of the distal end 106a of the guide sheath 106 and the crooked portion 158 relative to the guide pipe 104 and the position of the distal end 52a of the insertion portion 42 of the endoscope 18 relative to the distal end 106a of the guide sheath 106.

Therefore, the angle of the distal end 52a of the insertion portion 42 of the endoscope 18 to the central axis C can be changed in two stages by the two crooked portions: the crooked portion 66 of the insertion portion 42 and the crooked portion 158 of the guide sheath 106. Thus, the distal end 52a of the insertion portion 42 of the endoscope 18 can adjust the observation area from a narrow range inside the paranasal sinus to a wide range.

The crooked portion 66 of the insertion portion 42 of the endoscope 18 is protruded relative to the distal end 106a of the guide sheath 106. Thus, while protruding from the distal end 104a of the guide pipe 104, the distal end 52a of the insertion portion 42 of the endoscope 18 is bent in the crooked portion 158 of the sheath main body 152 of the guide sheath 106 and also bent in the crooked portion 66 of the insertion portion 42.

The first operation element 116 and the second operation element 118 are then turned in the same direction around the central axis C. That is, the press pad 198a of the interlock mechanism 190 is pressed to operate the first operation element 116 or the second operation element 118. In this instance, the distal end 52a of the insertion portion 42 moves to draw a circular-arc orbit on the crooked portion 158 of the guide sheath 106. The circular-arc orbit in this case is larger in diameter than the circular-arc orbit drawn on the crooked portion 66 of the insertion portion 42. Thus, a wide range in the paranasal sinus can be observed by performing this operation if necessary.

It is possible to adjust an observable range of the endoscope 18 by properly adjusting the position of the distal end 52a of the insertion portion 42 of the endoscope 18 relative to the distal end 106a of the guide sheath 106 and the position of the distal end 106a of the guide sheath 106 relative to the distal end 104a of the guide pipe 104.

When there is viscous matter in the paranasal sinus, the user confirms its color and amount on the monitor 16. When the viscous matter is sucked and removed, the user moves the second operation element 118 away from the first operation element 116 while maintaining the distal end 106a of the guide sheath 106 in the paranasal sinus as shown in FIG. 13. Thus, the distal end 52a of the insertion portion 42 of the endoscope 18 is pulled out of the guide pipe 104 through the distal end 106a of the guide sheath 106 and the distal end 104a of the guide pipe 104. In this instance, the distal end 52a of the insertion portion 42 is disposed between the pipeline 132a of the T-shaped pipe 132 and the O-ring 138b. That is, the insertion portion 42 of the endoscope 18 is pulled out of the guide sheath 106.

In this condition, the user actuates the suction source 22 to perform suction. The viscous matter passes in the guide sheath 106 through the distal end 106a of the guide sheath 106, and is sucked to the suction source 22 through the pipeline 132a of the T-shaped pipe 132 of the first operation element 116. In this instance, if the suction is possible even though the endoscope 18 remains inside the guide sheath 106, the suction may be performed in this situation without moving the second operation element 118.

After the suction source 22 is stopped, as shown in FIG. 14, the second operation element 118 is moved closer to the first operation element 116 to insert the distal end 52a of the insertion portion 42 of the endoscope 18 into the paranasal sinus beyond the distal end 106a of the guide sheath 106. The colors and conditions of the mucous membrane and the viscous matter in the paranasal sinus, and the amount of the viscous matter are again confirmed are then again confirmed on the monitor 16. In this instance, the first and second operation elements 116 and 118 are properly moved back and forth, and the first and second operation elements 116 and 118 are rotated to confirm the inside of the paranasal sinus. In particular, inflamed parts of the mucous membrane in the paranasal sinus are confirmed.

Thus, the user observes the inside of the paranasal sinus using the endoscope 18, and then diagnoses the state of the affected part.

(Step 3) The inside of the paranasal sinus is cleaned if necessary.

The user cleans the inside of the paranasal sinus if necessary.

A liquid such as a physiological saline is put into the paranasal sinus from the liquid supply source 24. If a greater amount of the supplied liquid is need, the distal end 52a of the insertion portion 42 is pulled out of the guide pipe 104 through the distal end 106a of the guide sheath 106 and the distal end 104a of the guide pipe 104 while the distal end 106a of the guide sheath 106 is maintained in the paranasal sinus, as shown in FIG. 13.

When the liquid is supplied from the liquid supply source 24 in this condition, a greater amount of liquid can be supplied than when the insertion portion 42 of the endoscope 18 is located inside the guide sheath 106. If the first operation element 116 is then turned, the range in which the liquid can be supplied by the crooked portion 158 of the guide sheath 106 is apparently wider than when the crooked portion 158 is not present. Thus, a wider range can be cleaned if the treatment instrument unit 12 is used.

After the inside of the paranasal sinus is cleaned with the physiological saline (cleaning liquid) in this way, the physiological saline containing the viscous matter is then sucked by the suction source 22.

The second operation element 118 is then again moved closer to the first operation element 116 to insert the distal end 52a of the insertion portion 42 of the endoscope 18 into the paranasal sinus beyond the distal end 106a of the guide sheath 106. The second operation element 118 is then properly turned, and the first operation element 116 is turned if necessary to confirm the color and amount of the mucous membrane in the paranasal sinus on the monitor 16.

When the viscous matter is remaining in the paranasal sinus, the viscous matter is sucked. When there is viscous matter that can not be sucked or when particular a mucous membrane tissue needs to be extracted, the distal end 52a of the insertion portion 42 is pulled out of the guide pipe 104 while the distal end 106a of the guide sheath 106 is maintained in the paranasal sinus. The pin 164 disposed in the plane 46a of the support portion 46 of the endoscope 18 is then removed to remove the insertion portion 42 of the endoscope 18 from the treatment instrument 20. A forceps or a brush, for example, is put through the guide sheath 106 from the proximal side of the T-shaped pipe 132, and the distal end 106a of the guide sheath 106 is inserted into the paranasal sinus beyond the distal end 106a of the guide sheath 106. In this condition, the mucous membrane tissue may be extracted by, for example, the forceps or the brush. The forceps or the brush can also be used instead of suction to collect the viscous matter.

(Step 4) The inside of the paranasal sinus is treated. For example, medicine is administered to the affected part in the paranasal sinus.

The forceps or the brush, for example, are removed from the treatment instrument 20, and the insertion portion 42 of the endoscope 18 is again attached to the treatment instrument 20.

The guide sheath 106 and the insertion portion 42 of the endoscope 18 are properly moved to confirm the affected part.

The chemical is stuck to the affected part from the liquid supply source 24 through the space between the inner circumferential surface of the guide sheath 106 and the outer circumferential surface of the insertion portion 42.

In this instance, the chemical to be supplied is, for example, steroid and/or an antibacterial agent. Moreover, the supplied chemical is preferably retained in the paranasal sinus after the supply. To supply the chemical, for example, a medicine such as steroid and/or an antibacterial agent is contained in temperature-responding gel which increases viscosity at about the body temperature. Since the chemical increases viscosity after supplied, the chemical can be in touch with the affected part for a long time. The chemical is then retained in the paranasal sinus so that the effect of the chemical can be longer. More simply, it is also possible to produce a similar effect by inserting a piece of fine gauze into the paranasal sinus and containing the chemical therein or by putting a lid on the opening of the paranasal sinus. It is also possible to blend the chemical with a biodegradable material and gradually dissolving the chemical to keep the effect.

The treatment instrument unit 12 according to this embodiment has the two crooked portions 66 and 158. Thus, the range in which the distal end 52a of the insertion portion 42 can be directed can be wider than when the insertion portion 42 of the endoscope 18 alone has the crooked portion. Therefore, it is possible to further ensure that the affected part, that is, the inside of the paranasal sinus can be observed and that the chemical can be administered or sprayed to the affected part.

If necessary, the chemical is administered to the affected part while the insertion portion 42 of the endoscope 18 is pulled out of the guide sheath 106.

(Step 5) The treatment instrument unit 12 of the treatment system 10 is pulled out of the paranasal sinus.

The first and second operation elements 116 and 118 are moved toward the proximal end 112b of the main body 112 of the handle unit 102. Thus, the distal end 52a of the insertion portion 42 of the endoscope 18 and the distal end 106a of the guide sheath 106 are pulled out of the paranasal sinus. The distal end 106a of the guide sheath 106 and the distal end 52a of the insertion portion 42 of the endoscope 18 are then retracted relative to the distal end 104a of the guide pipe 104. When the balloon 176 is inflated, the balloon 176 is deflated.

The guide pipe 104 is separated from the entrance of the paranasal sinus and then pulled out of the nostril with the greatest possible effort to prevent the distal end 104a of the bent pipe 172 of the guide pipe 104 disposed at the entrance of the paranasal sinus from abutting on the mucous membrane tissue inside the nose.

After the end of a series of treatments, the user pulls out the pin 164 disposed in the plane 46a of the support portion 46 of the endoscope 18, and then removes the endoscope 18 from the treatment instrument 20. The endoscope 18 is then cleaned, disinfected, and sterilized to be reusable. On the other hand, the treatment instrument 20 may be disassembled and then cleaned, disinfected, and sterilized to be reusable or may be simply disposed of.

As described above, the following can be said according to the treatment system 10 in this embodiment.

The treatment instrument unit 12 that combines the endoscope 18 and the treatment instrument 20 is used to display the observation image on the monitor 16, and the user can certainly dispose the distal end 104a of the guide pipe 104, for example, at the entrance of the paranasal sinus while viewing the observation image. In this instance, the endoscope 18 is used, so that the user (doctor) can easily recognize the situation in the insertion path (e.g. the condition of the mucous membrane in the nose). Moreover, the endoscope 18 is used, so that it is possible to safely and certainly recognize whether a desired paranasal sinus is accessed.

Therefore, by using the treatment instrument unit 12 according to this embodiment, the distal end 104a of the guide pipe 104 can safely and certainly access the entrance of the paranasal sinus while directly recognizing the situation in the path from the external nostril to the paranasal sinus by the observation image.

The distal end 104a of the guide pipe 104 is made of a rigid material such as stainless steel, and the elastic portion 174b is provided in the straight pipe 174. Alternatively, the whole guide pipe 104 is made of an elastic part having certain flexibility. Therefore, even if excessive force is applied when the guide pipe 104 is in collision with the entrance of the paranasal sinus, the elastic portion 174b bends so that it is possible to prevent any load from being applied to the mucous membrane and bone around the opening of the paranasal sinus.

In the treatment using the endoscopic treatment system 10 according to this embodiment, the insertion portion 42 of the endoscope 18 is flexible. Thus, when the distal end 52a of the insertion portion 42 of the endoscope 18 is introduced into the paranasal sinus, it is not necessary to cut the entrance to the paranasal sinus, crush the part around the entrance, or enlarge the entrance. According to this embodiment, the balloon 176 provided at the distal end 172a of the guide pipe 104 is inflated in the vicinity of the entrance of the paranasal sinus. The guide pipe 104 only holds the position relative to the entrance of the paranasal sinus. Therefore, when a treatment using the treatment system 10 according to this embodiment is conducted, it is possible to significantly reduce invasion of the patient.

The treatment instrument unit 12 according to this embodiment directly inserts the distal end 52a of the insertion portion 42 of the endoscope 18 into the paranasal sinus through the distal end 104a of the guide pipe 104. Thus, the user can easily recognize the situation in the paranasal sinus. Therefore, it is possible to visually diagnose the condition of the inflammation of the mucous membrane in the paranasal sinus.

The crooked portions 66 and 158 are formed in both the distal end 42a of the insertion portion 42 of the endoscope 18 and distal end 152a of the guide sheath 106. Thus, a wider range can be obtained as the observation image on the endoscope 18 than when one of the crooked portions is present. Thus, it is possible to inhibit the movements of the guide sheath 106 and the insertion portion 42 of the endoscope 18 along the central axis C to the minimum.

In particular, the crooked portion 158 is formed in the guide sheath 106 which is more persevering and more unbendable than the endoscope 18. Thus, the observation direction of the observation optical system 64 of the insertion portion 42 can be faced in a proper direction by the guide sheath 106. A narrowed part can be observed by the endoscope 18 and simultaneously passed by the guide sheath 106 while the positional relation between the insertion portion 42 of the endoscope 18 and the guide sheath 106 is maintained. Owing to the crooked portion 158 of the guide sheath 106, suction can be easily performed in a wide range, and water supply (cleaning) and medication can be easily performed in a wide range while the insertion portion 42 of the endoscope 18 is pulled out of the guide sheath 106.

When the crooked portions 66 and 158 have the same shape and the guide sheath 106 and the insertion portion 42 of the endoscope 18 overlap in the part of the same shape, the rigidity of the inserted part in which the insertion portion 42 of the endoscope 18 is adapted to the guide sheath 106 is higher than when each of these components is a single component. Thus, the rotations of the guide sheath 106 and the insertion portion 42 of the endoscope 18 around the central axis C and their operability during insertion and removal improve.

The indexes 182a, 182b, 184a, 184b, and 186 are properly formed in the main body 112 of the handle unit 102 and the first and second operation elements 116 and 118. Thus, by recognizing the positional relation of the operation elements 116 and 118 to the main body 112 of the handle unit 102, the user can easily recognize the position and pose (the direction brought to by the crooked portion 158) of the distal end 106a of the guide sheath 106 and the position and pose (the direction brought to by the crooked portion 66) of the distal end 52a of the insertion portion 42 of the endoscope 18 relative to the distal end of the guide pipe 104.

Thus, the indexes 184a, 184b, and 186 of the handle unit 102 allow the user to recognize the axial position of the distal end 106a of the guide sheath relative to the distal end 104a of the guide pipe 104 and the circumferential position of the distal end 106a of the guide sheath 106 relative to the distal end 104a of the guide pipe 104. The indexes 182a and 182b of the handle unit 102 allow the user to recognize the axial position of the distal end 52a of the insertion portion 42 relative to the distal end 104a of the guide pipe 104 and the circumferential position of the distal end 52a of the insertion portion 42 relative to the distal end 104a of the guide pipe 104. In other words, the indexes 182a and 184a of the first operation element 116 allow the user to recognize the axial position of the distal end 106a of the guide sheath 106 relative to the distal end 104a of the guide pipe 104 and the circumferential position of the distal end 106a of the guide sheath 106 relative to the distal end 104a of the guide pipe 104. The indexes 182b and 184b of the second operation element 118 allow the user to recognize the axial position of the distal end 52a of the insertion portion 42 relative to the distal end 104a of the guide pipe 104 and the circumferential position of the distal end 52a of the insertion portion 42 relative to the distal end 104a of the guide pipe 104. The user can then recognize that the bending directions of the crooked portions 66 and 158 correspond to each other when the first index 182a of the first operation element 116 and the second index 182b of the second operation element 118 are at the same circumferential position. Moreover, the user can recognize that the crooked portions 66 and 158 correspond to each other when the index 184a of the first operation element 116 and the index 184b of the second operation element 118 are respectively located at predetermined axial positions (positions located at a distance) relative to the main body 112 of the handle unit 102.

The interlock mechanism 190 can be properly used to switch between the interlocked state and the non-interlocked state. Therefore, in the interlocked state, one of the first and second operation elements 116 and 118 can only be operated to move the guide sheath 106 and the insertion portion 42 of the endoscope 18 in the same direction. Thus, it is possible to reduce the number of times of operations in which the user alternately moves the two operation elements 116 and 118 little by little.

The endoscopic treatment instrument 20 according to this embodiment is used together with the endoscope 18 including the insertion portion 42 which is flexible and through which the observation optical system 64 is inserted. The treatment instrument 20 includes the guide pipe 104 which has the first distal end 104a and through which the insertion portion 42 is inserted so that the distal end 52a of the insertion portion 42 and the distal side of the first distal end 104a are observable through the first distal end 104a by the observation optical system 64 or so that the distal side of the distal end 52a of the insertion portion 42 is observable by the observation optical system 64 while the distal end 52a of the insertion portion 42 is protruded relative to the first distal end 104a, and the guide sheath 106 which has the second distal end 106a and which has an inside diameter to insert the insertion portion 42 therethrough so that the distal end 52a of the insertion portion 42 is configured to protrude relative to the second distal end 106a and which is inserted through the guide pipe 104 so that the second distal end 106a is configured to protrude relative to the first distal end 104a of the guide pipe 104. Thus, by using the treatment instrument 20 according to this embodiment together with the endoscope 18, it is possible to safely and certainly cause the distal end 104a of the guide pipe 104 to access the entrance of the paranasal sinus while recognizing the situation in the path from the external nostril to the paranasal sinus by the observation image. Moreover, by using the treatment instrument 20 together with the endoscope 18, it is possible to directly observe the symptom of each part in the paranasal sinus and conduct a treatment.

Figure 15:
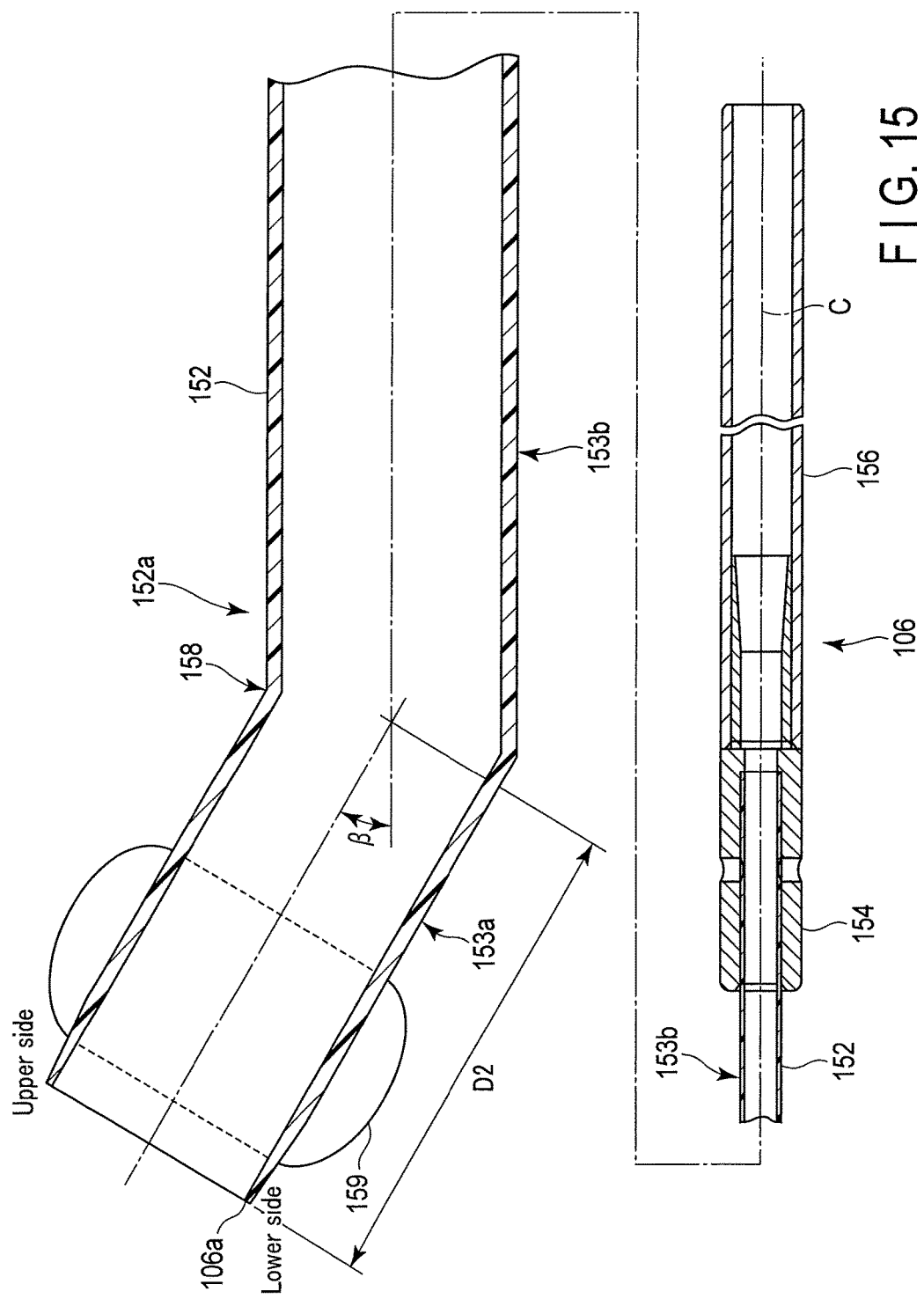
FIG. 15 is a schematic longitudinal sectional view showing a guide sheath of the treatment instrument unit of the treatment system according to a modification of the first embodiment.

As shown in FIG. 15, a balloon 159 may be disposed on the outer circumferential surface of the first area 153a of the sheath main body 152 of the guide sheath 106. For example, when a patient has a narrow path in the opening of the paranasal sinus, the path can be expanded by this balloon as needed to insert the insertion portion 42 of the endoscope 18. The balloon 159 is expanded at a pressure of about 8 to 12 atmosphere by a liquid or a gas through a separately provided balloon expanding lumen.

Figure 16A:
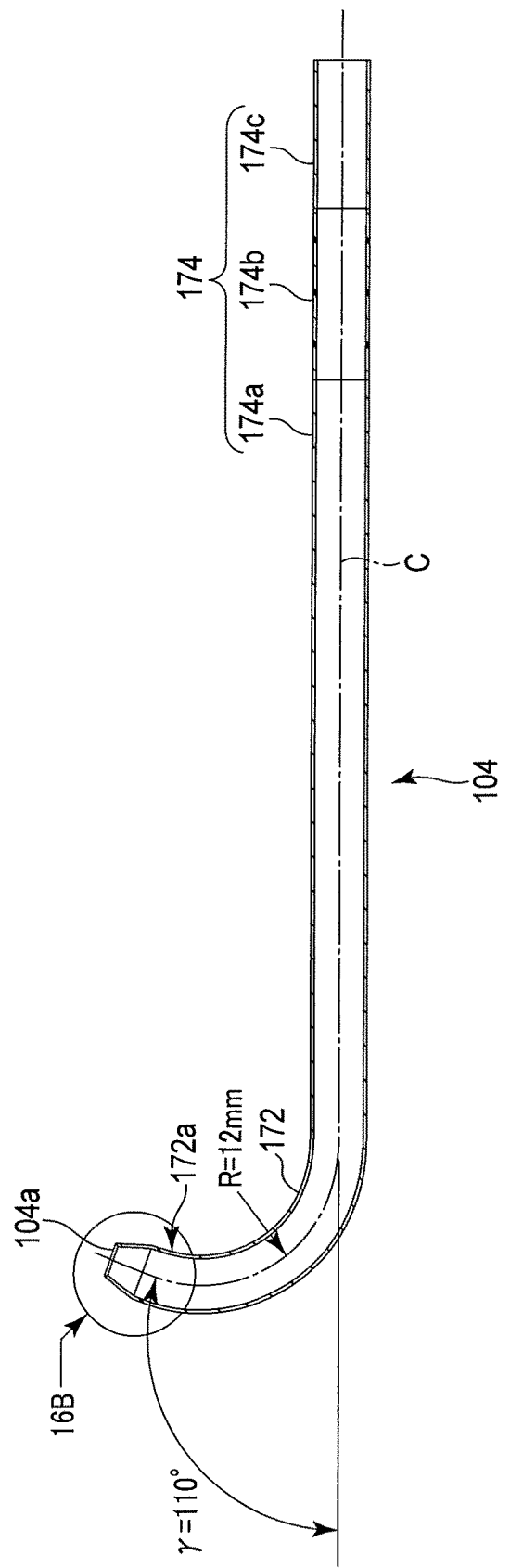
FIG. 16A is a schematic longitudinal sectional view showing a guide pipe of the treatment instrument unit of the treatment system according to a modification of the first embodiment.

The shape of the bent pipe 172 of the guide pipe 104 according to this embodiment can be changed suitably to the treatment target. As shown in FIG. 16A, the angle γ of the bent pipe 172 to the straight pipe 174 of the guide pipe 104 is, for example, about 110°. This angle γ is greater than the angle γ of the bent pipe 172 to the straight pipe 174 of the guide pipe 104 shown in FIG. 8A. The guide pipe 104 shown in FIG. 16A is preferably used to treat, for example, the maxillary sinus of the paranasal sinus. The inside diameter and bending radius R (e.g. about 5 to 25 mm) of the bent pipe 172 of the guide pipe 104 are set in consideration of the length (rigid length) from the distal end 52a of the distal hard portion 52 of the insertion portion 42 of the endoscope 18 to the proximal side along the central axis C when the sheath main body 152 of the guide sheath 106 is disposed on the outer circumference. Here, to perform an observation by the endoscope 18, the guide pipe 104 has its inside diameter larger than when a simple guide wire or light guide fiber is used. Moreover, the inside diameter of the straight pipe 174 in particular can be smaller than the inside diameter of the bent pipe 172, but is substantially the same inside diameter to more effectively perform suction performance.

The paranasal sinus which is the treatment target for the treatment instrument unit 12 of the treatment system (endoscopic system) 10 according to this embodiment is not limited to the frontal sinus or the maxillary sinus.

The straight pipe 174 of the guide pipe 104 shown in FIG. 16A is also made of a combination of a rigid material such as a metal (e.g. stainless steel or aluminum alloy material) or a rigid resin (e.g. polyethylene (PE) or polypropylene (PP)) and a flexible material such as silicone or a nylon material, similarly to the guide pipe 104 shown in FIG. 8A. The straight pipe 174 has the distal rigid portion 174a, the elastic portion 174b, and a proximal rigid portion 174c. Here, the part of the straight pipe 174 from the proximal end of the rigid portion 174a (the distal end of the elastic portion 174b) to the distal end of the bent pipe 172 is seamlessly formed. The elastic portion 174b may be formed at any position between the distal end and proximal end of the straight pipe 174. Owing to such an elastic portion 174b, if, for example, the bent pipe 172 abuts on a living tissue, the straight pipe 174 is elastically deformed in the elastic portion 174b. Both the sheath main body 152 of the guide sheath 106 disposed inside the guide pipe 104 and the flexible pipe 54 of the insertion portion 42 of the endoscope 18 are flexible. Thus, it is possible to prevent any load from being applied to the living tissue by the guide pipe 104.

The adapter 175 is fixed to the guide pipe 104 shown in FIG. 16A on the outer circumferential surface of the proximal end of the proximal rigid portion 174c. The balloon 176 may be formed as a circumferential projection made of a material such as rubber.

Figure 16B:
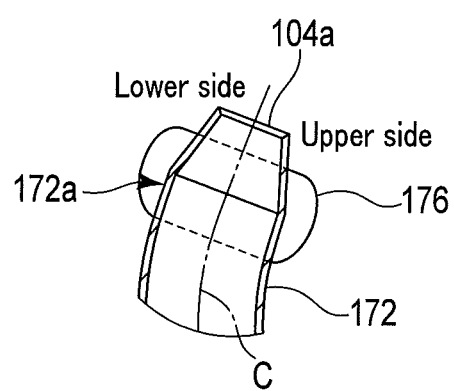
FIG. 16B is a schematic enlarged view showing the distal end of the bent pipe of the guide pipe indicated by the reference sign 16B in FIG. 16A.

As shown in FIG. 16B, the balloon 176 which functions in a manner similar to the balloon 176 shown in FIG. 8C is preferably provided.

Next, the second embodiment is described with reference to FIG. 17 and FIG. 18. This embodiment is a modification of the first embodiment, and the same components as the components described in the first embodiment or components having the same functions are provided with the same signs as much as possible, and are not described here.

Figure 17:
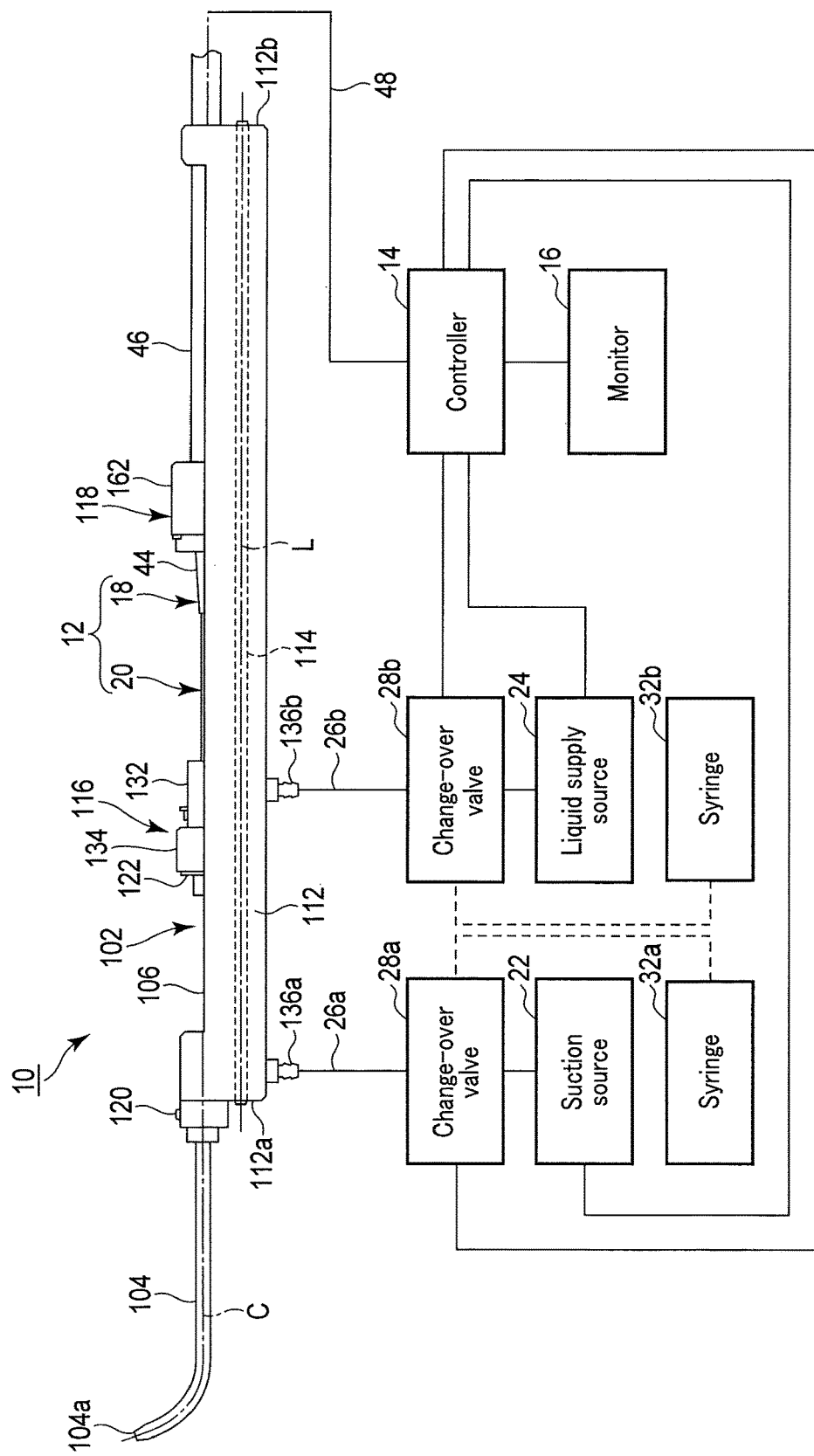
FIG. 17 is a schematic diagram of a treatment system according to a second embodiment.
Figure 18:
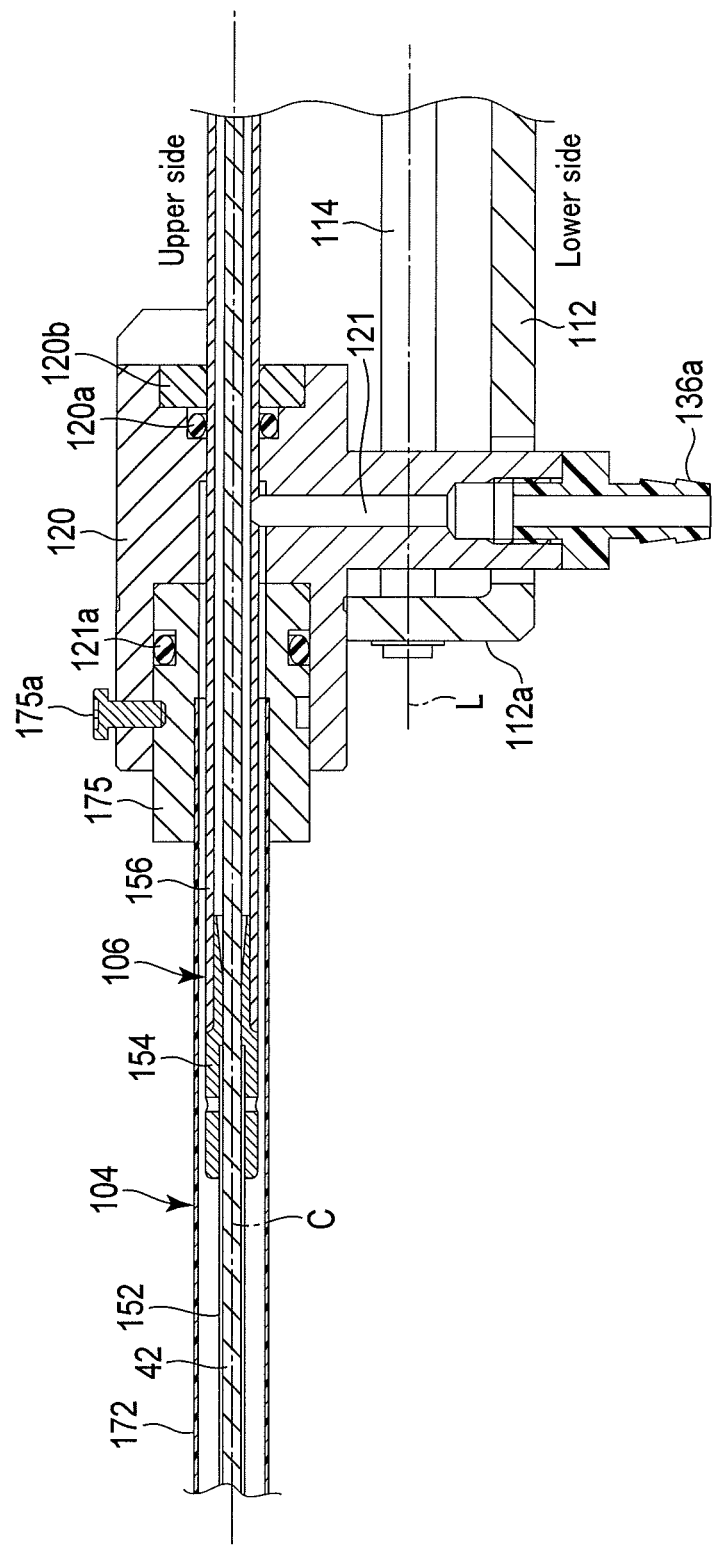
FIG. 18 is a schematic longitudinal sectional view showing, in an enlarged form, the endoscopic treatment instrument unit in the vicinity of a connection pipe.

As shown in FIG. 17 and FIG. 18, the treatment instrument 20 according to this embodiment has two joints 136a and 136b. As shown in FIG. 17, a change-over valve 28a and the suction source 22 are connected to the first joint 136a in order. A change-over valve 28b and the liquid supply source 24 are connected to the second joint 136b in order.

The change-over valve 28a, for example, a three-way cock is provided between the end of a tube 26a extending from the first joint 136a of the treatment instrument 20 and the suction source 22. A syringe 32a, for example, can be connected to the change-over valve 28a. The change-over valve 28b, for example, a three-way cock is provided between the end of a tube 26b extending from the second joint 136b of the treatment instrument 20 and the liquid supply source 24. A syringe 32b, for example, can be connected to the change-over valve 28b. The change-over valves 28a and 28b may be electromagnetically operated by turning an unshown switch connected to the controller 14 or may be manually switched.

As shown in FIG. 18, the joint 136a which communicates with the central axis C of the connection pipe 120 through a pipeline 121 is connected to the connection pipe 120. The joint 136a protrudes downward from the main body 112 of the handle unit 102. The first joint 136a is in communication with the space between the inner circumferential surface of the guide pipe 104 and the outer circumferential surface of the guide sheath 106. The first joint 136a is connected to the suction source 22, and is mainly used to suck a tissue such as viscous matter.

The adapter 175 is fixed to the proximal end of the proximal rigid portion 174c of the straight pipe 174 of the guide pipe 104. The adapter 175 is fixed to the connection pipe 120 by, for example, the fixed element 175a.

The O-ring 121a is provided between the connection pipe 120 and the adapter 175 of the guide pipe 104. Thus, the space between the guide pipe 104 and the adapter 175 is sealed. Therefore, owing to the O-rings 120a and 121a, an object to be sucked is sucked through the pipeline 121 and the joint 136a as a result of the suction by the suction source 22.

The second joint 136b shown in FIG. 17 is formed in the same manner as the joint 136 described in the first embodiment. That is, the second joint 136b is in communication with the space between the outer circumferential surface of the insertion portion 42 of the endoscope 18 and the inner circumferential surface of the guide sheath 106. The second joint 136b is connected to the liquid supply source 24, and is mainly used to supply a liquid, for example, for cleaning with the physiological saline.

Suction and liquid supply can be simultaneously performed by use of the treatment system 10 according to second embodiment. Thus, it is not necessary to switch between suction and liquid supply during a treatment, and the treatment time can be reduced.

Other structures and functions are similar to those described in the first embodiment, and are not described here.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscopic treatment instrument configured to be used with an endoscope including an insertion portion that includes an observation optical system, the endoscopic treatment instrument comprising:
    a guide pipe that has a first distal end and is configured to receive the insertion portion therethrough so that an area in front of a distal end of the insertion portion and an area in front of the first distal end of the guide pipe are observable through the first distal end by the observation optical system or so that the area in front of the distal end of the insertion portion is observable by the observation optical system while the distal end of the insertion portion is protruded relative to the first distal end; and
    a guide sheath including:
        a second distal end,
        an inside diameter configured to receive the insertion portion therethrough so that the distal end of the insertion portion can protrude relative to the second distal end, the guide sheath being inserted through the guide pipe so that the second distal end of the guide sheath can protrude relative to the first distal end of the guide pipe, and
        a crooked portion having a pre-formed bend positioned at a distance from the second distal end of the guide sheath in a proximal direction, the crooked portion of the guide sheath being configured to be more rigid than a pre-formed crooked portion of the insertion portion.

2. The treatment instrument according to claim 1, wherein the guide sheath is turnable relative to the guide pipe such that the second distal end draws a circular-ring orbit in response to turning of the guide sheath.

3. The treatment instrument according to claim 1, further comprising a handle unit that is configured to be grasped by a user, and includes a first operation element that is configured to move the guide sheath in an axial direction relative to the guide pipe and the insertion portion, and is turnable around its axis.

4. The treatment instrument according to claim 3, wherein the handle unit has an index which allows the user to recognize:
    an axial position of the second distal end of the guide sheath relative to the first distal end of the guide pipe, and a circumferential position of the second distal end of the guide sheath relative to the first distal end of the guide pipe.

5. The treatment instrument according to claim 3, wherein the handle unit further includes a second operation element that is configured to move the insertion portion in the axial direction relative to the guide pipe and the guide sheath, and is turnable around its axis.

6. The treatment instrument according to claim 5, wherein the handle unit has an index which allows the user to recognize:
   an axial position of the distal end of the insertion portion relative to the first distal end of the guide pipe, and
   a circumferential position of the distal end of the insertion portion relative to the first distal end of the guide pipe.

7. The treatment instrument according to claim 1, further comprising a handle unit which is configured to be grasped by a user and includes:
   a first operation element configured to move the guide sheath relative to the guide pipe and the insertion portion; and
   a second operation element which is operable to move the insertion portion relative to the guide pipe and the guide sheath, and which is operable together with the first operation element.

8. The treatment instrument according to claim 1, wherein the guide pipe includes:
   a bent pipe portion having the first distal end at its distal end portion, and
   a straight pipe portion provided at a proximal end of the bent pipe, at least part of the straight pipe portion being elastically deformable.

9. A treatment instrument unit comprising:
   an endoscope including an insertion portion having flexibility and an observation optical system; and
   the treatment instrument according to claim 1 through which the insertion portion is inserted relative to the guide pipe and the guide sheath.

10. The treatment instrument unit according to claim 9, wherein:
    the insertion portion includes:
      a distal hard portion formed at its distal end, and
      a flexible pipe portion formed on a proximal side of the distal hard portion, and
    the guide pipe includes:
      a straight pipe portion through which the guide sheath is movable while the insertion portion is inserted through the guide sheath, and
      a bent pipe portion which is located on a distal side of the straight pipe and which has an inside diameter and a bending radius that permit the distal hard portion of the insertion portion to protrude on the distal side through the first distal end while the insertion portion is inserted through the guide sheath.

11. The treatment instrument unit according to claim 9, wherein the insertion portion has a first crooked portion having a pre-formed bend positioned at a first distance from its distal end in the proximal direction.

12. The treatment instrument unit according to claim 11, further comprising a handle unit which includes:
    a first operation element which is configured to move the guide sheath in an axial direction relative to the guide pipe and the insertion portion, and which is turnable around its axis,
    a second operation element which is configured to move the insertion portion in the axial direction relative to the guide pipe and the guide sheath, and which is turnable around its axis, and
    a first index which allows a user to recognize:
      an axial position of the distal end of the insertion portion relative to the first distal end of the guide pipe, and
      a circumferential position of the distal end of the insertion portion relative to the first distal end of the guide pipe.

13. The treatment instrument unit according to claim 12, wherein:
    the handle unit includes a second index which allows the user to recognize:
      an axial position of the second distal end of the guide sheath relative to the first distal end of the guide pipe, and
      a circumferential position of the second distal end relative to the first distal end of the guide pipe, and
    the crooked portion of the guide sheath is bent in an identical direction to that of the first crooked portion of the insertion portion when the first index and the second index are located at the same circumferential position.

14. The treatment instrument unit according to claim 12, wherein the first distal end of the guide pipe is aligned with the distal end of the insertion portion of the endoscope when the first index is located at a predetermined position relative to the handle unit.

15. The treatment instrument unit according to claim 9, wherein the insertion portion includes a first crooked portion having a pre-formed bend positioned at a first distance from its distal end in the proximal direction.

16. The treatment instrument unit according to claim 15, further comprising a handle unit which includes:
    a first operation element which is configured to move the guide sheath in an axial direction relative to the guide pipe and the insertion portion, and which is turnable around its axis,
    a first index which allows a user to recognize:
      an axial position of the second distal end of the guide sheath relative to the first distal end of the guide pipe, and
      a circumferential position of the second distal end relative to the first distal end of the guide pipe, and
    a second operation element which is configured to move the insertion portion in the axial direction relative to the guide pipe and the guide sheath and which is turnable around its axis.

17. The treatment instrument unit according to claim 16, wherein:
    the handle unit further includes a second index which allows the user to recognize:
      an axial position of the distal end of the insertion portion relative to the first distal end of the guide pipe, and
      a circumferential position of the distal end of the insertion portion relative to the first distal end of the guide pipe, and
    the crooked portion of the guide sheath is bent in an identical direction to that of the first crooked portion of the insertion portion when the first index and the second index are located at the same circumferential position.

18. The treatment instrument unit according to claim 17, wherein the distal end of the insertion portion of the endoscope is aligned with the second distal end of the guide sheath when each of the first index and the second index is located at a predetermined axial position relative to the handle unit.

19. The treatment instrument unit according to claim 15, wherein the distance between the crooked portion of the guide sheath and the second distal end of the guide sheath is equal to the first distance between the first crooked portion of the insertion portion and the distal end of the insertion portion.

20. The treatment instrument unit according to claim 9, wherein the guide pipe includes:
    a bent pipe portion, and
    a straight pipe portion which is: (i) provided at a proximal end of the bent pipe portion, (ii) at least partly elastically deformable, and (iii) more rigid than the insertion portion of the endoscope and the guide sheath.

21. A treatment system comprising:
    the treatment instrument unit according to claim 9; and
    a controller which is connected to the endoscope of the treatment instrument unit and is configured to control the observation optical system.

22. The treatment instrument unit according to claim 9, further comprising a handle unit which is configured to be grasped by a user and includes:
    a first operation element which is configured to move the guide sheath relative to the guide pipe and the insertion portion; and
    a second operation element which is operable to move the insertion portion relative to the guide pipe and the guide sheath, and which is operable together with the first operation element.

23. The treatment instrument according to claim 1, wherein the pre-formed bend of the crooked portion of the guide sheath is an angular bend.

24. The treatment instrument according to claim 1, wherein the guide sheath is configured to be changed between:
    an interlocked state in which the guide sheath is configured to move together with the insertion portion relative to the guide pipe, and
    a non-interlocked state in which the guide sheath is moveable independently of the insertion portion relative to the guide pipe.

* * * * *